United States Patent
Biagini et al.

(10) Patent No.: US 6,984,703 B1
(45) Date of Patent: Jan. 10, 2006

(54) BRIDGED METALLOCENE COMPOUNDS AS OLEFIN-POLYMERIZATION CATALYSTS

(75) Inventors: Paolo Biagini, Trecate (IT); Roberto Santi, Novara (IT); Giuliana Schimperna, Novara (IT); Maria Caldararo, Trecate (IT); Giampietro Borsotti, Novara (IT); Francesco Masi, Sant'Angelo Lodigiano (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/148,571

(22) PCT Filed: Nov. 27, 2000

(86) PCT No.: PCT/EP00/11824

§ 371 (c)(1),
(2), (4) Date: Aug. 20, 2002

(87) PCT Pub. No.: WO01/40238

PCT Pub. Date: Jun. 7, 2001

(30) Foreign Application Priority Data

Dec. 3, 1999 (IT) .......................... MI99A002536

(51) Int. Cl.
*C08F 4/42* (2006.01)

(52) U.S. Cl. ...................... 526/160; 526/943; 526/348; 502/103; 502/152; 556/51; 556/52; 556/53

(58) Field of Classification Search ............... 502/152, 502/103; 526/160, 943, 348; 556/51, 52, 556/53

See application file for complete search history.

(56) References Cited

U.S. PATENT DOCUMENTS 5,504,172 A * 4/1996 Imuta et al. ................ 526/351

FOREIGN PATENT DOCUMENTS

| EP | 0 672 675 | | 9/1995 |
| WO | WO 94/11406 | * | 5/1994 |
| WO | WO 96/38458 | * | 12/1996 |

* cited by examiner

*Primary Examiner*—Ling-Sui Choi
(74) *Attorney, Agent, or Firm*—Oblon, Spivak, McClelland, Maier & Neustadt, P.C.

(57) ABSTRACT

The present invention relates to metallocene compounds consisting of indenyl-cyclopentadienyl groups non-symmetrically joined by a bivalent radical. Said compounds can be conveniently used as components of catalysts for the polymerization of olefins.

34 Claims, No Drawings

BRIDGED METALLOCENE COMPOUNDS AS OLEFIN-POLYMERIZATION CATALYSTS

The present invention relates to bridged metallocene compounds, the corresponding ligands, a process for their preparation and the use of said compounds as components of catalysts for the polymerization of olefins.

More specifically, the invention relates to metallocene compounds consisting of indenyl-cyclopentadienyl groups, non-symmetrically joined by a bivalent radical.

It is known that metallocene compounds can be used in various reactions of industrial interest.

For example, chiral, stereo rigid metallocene compounds consisting of two bridged indenyl groups and a metal such as zirconium, are known and used as components of catalysts for the polymerization of olefins and, in particular, for the preparation of stereo-regular polyolefins.

In these metallocenes, the indenyl groups are joined by means of bivalent radicals which have two or more carbon atoms, such as —$(CH_2)_2$ groups or with atoms different from carbon.

These radicals are generally bound in different positions relating to the ring with five carbon atoms of both indenyl groups, as described in patent applications EP-A-485,823, EP-A-372,414, WO 94/11406.

Metallocenes are also known, whose indenyl groups are joined by means of bivalent radicals bound in position 4 of the ring with six carbon atoms of both indenyl groups, as described in patent applications EP 693 502, WO 96/38458.

New metallocene compounds have now been found in which the bivalent radical is bound to the ring with five carbon atoms of a cyclopentadienyl, indenyl, fluorenyl group and to the ring with six carbon atoms of an indenyl group, which can be conveniently used as components of catalysts for the polymerization of olefins.

An object of present invention relates, in particular, to metallocene compounds having general formula (I):

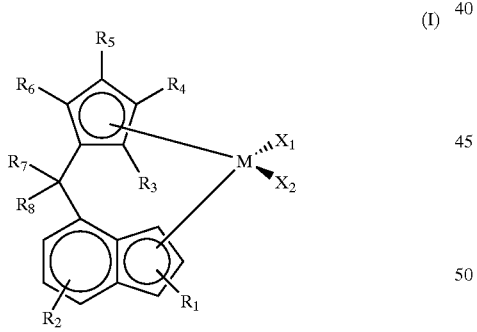

(I)

wherein:
$R_1$ and $R_2$ can independently occupy any of the free positions of the indene group;
$R_1$, $R_2$, $R_3$, $R_4$, $R_5$, $R_6$, $R_7$ and $R_8$ independently represent hydrogen, halogen, preferably F, Cl or Br, a linear or branched, saturated or unsaturated, cycloaliphatic or aromatic $C_1$–$C_{20}$ hydrocarbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements, preferably Si, O, N, S, P; in addition, any two, or both pairs, of the substituents $R_3$, $R_4$, $R_5$ and $R_6$, adjacent to each other, are joined to each other to form a saturated or unsaturated $C_4$–$C_{20}$ cyclic structure, comprising a bond of the cyclopentadienyl ring, said structure optionally containing one or more of the heteroatoms specified above;

M represents a metal selected from titanium, zirconium or hafnium;

$X_1$ and $X_2$ each independently represent a group of an anionic nature bound to the metal M.

Typical examples of $X_1$ and $X_2$ are hydride, halide, preferably chloride, a linear or branched alkyl group, such as methyl, ethyl, butyl, isopropyl, isoamyl, octyl decyl benzyl allyl, methyl-allyl, a cycloalkyl group such as cyclopentyl, cyclohexyl, 4-methylcyclohexyl, an aryl group, such as phenyl or toluyl, an alkoxyl or thioalkoxyl group, such as methoxyl, ethoxyl, iso- or sec-butoxyl, ethylsulfide, a carboxyl group, such as acetate, propionate, butyrate pivalate, versatate, naphthenate, or again, a dialkylamide group, such as diethylamide, dibutylamide, or an alkylsilylamide group, such as bis(trimethylsilyl)amide.

$X_1$ and $X_2$ can also be chemically bound to each other and form a cycle having from 4 to 7 different hydrogen atoms, also comprising the metal M.

Typical examples of this aspect are divalent anionic groups such as the trimethylene or tetramethylene group, or the ethylenedioxy group.

The metallocene compounds of the present invention can exist in isomeric, racemic or meso forms.

A further object of the present invention relates to compounds having general formula (Ia) which are used for the preparation of the compounds having general formula (I):

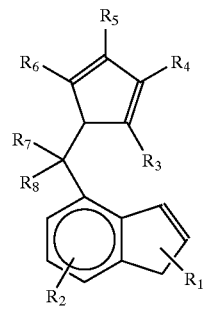

(Ia)

wherein:
$R_1$, $R_2$, $R_3$, $R_4$, $R_5$, $R_6$, $R_7$ and $R_8$ have the meanings defined above.

Examples of structures of compounds having general formula (Ia), are indicated in Table 1 below:

TABLE 1

Examples of structures of compounds with general formula

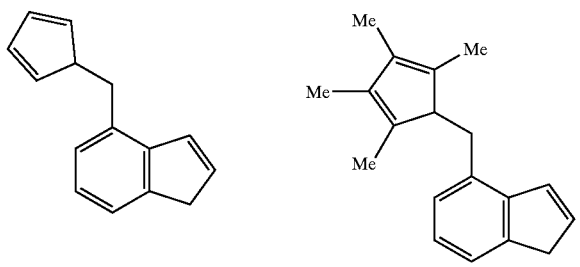

TABLE 1-continued
Examples of structures of compounds with general formula
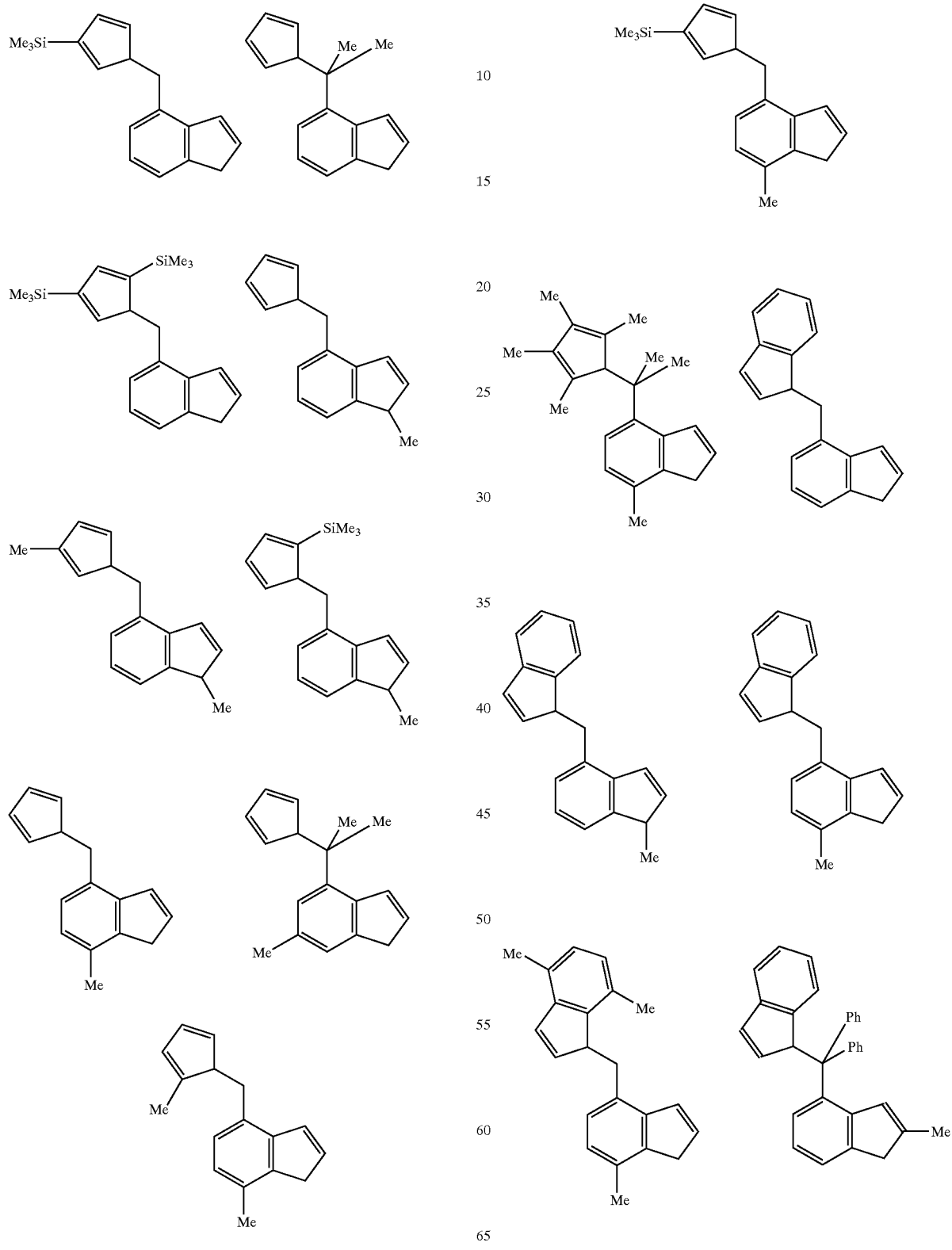

TABLE 1-continued
Examples of structures of compounds with general formula
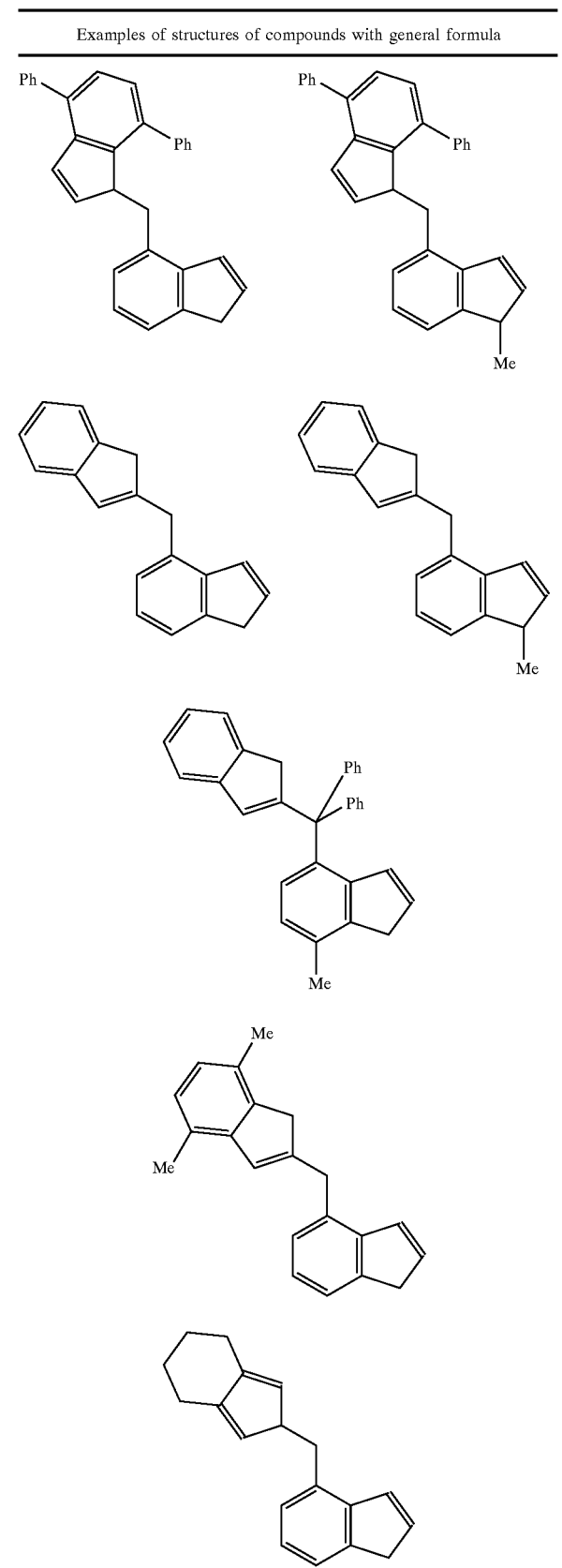
TABLE 1-continued
Examples of structures of compounds with general formula
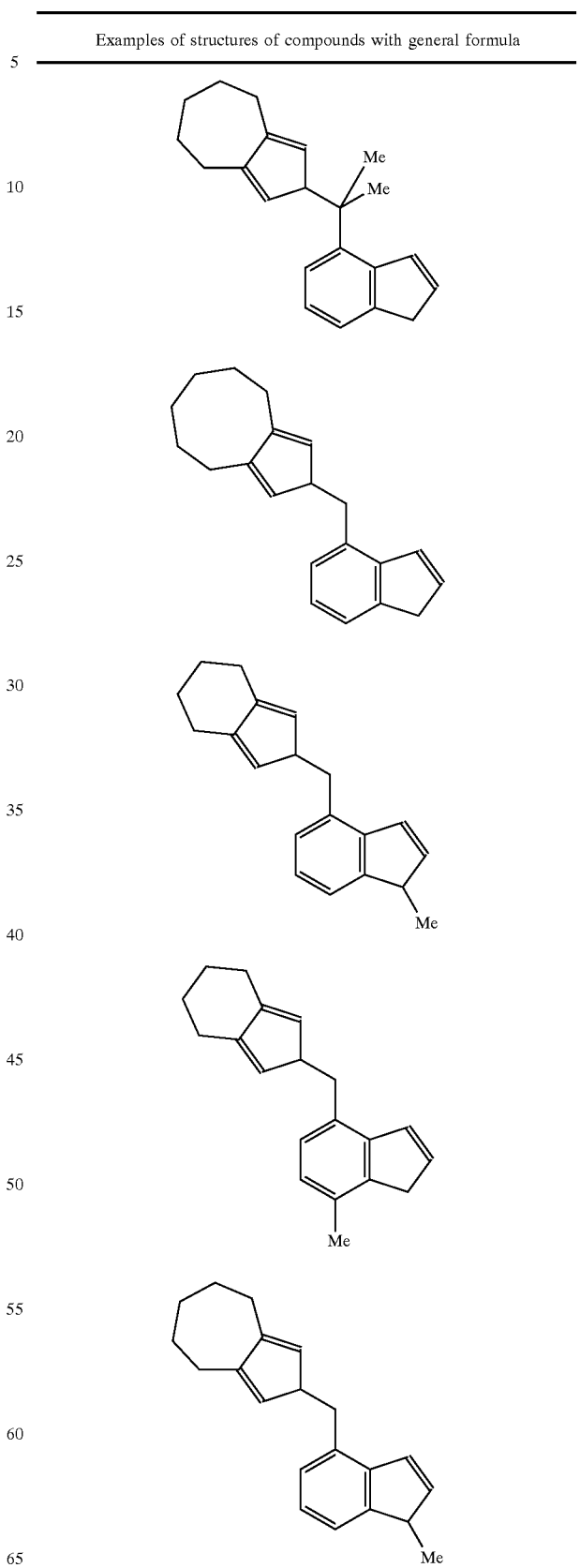

TABLE 1-continued

Examples of structures of compounds with general formula

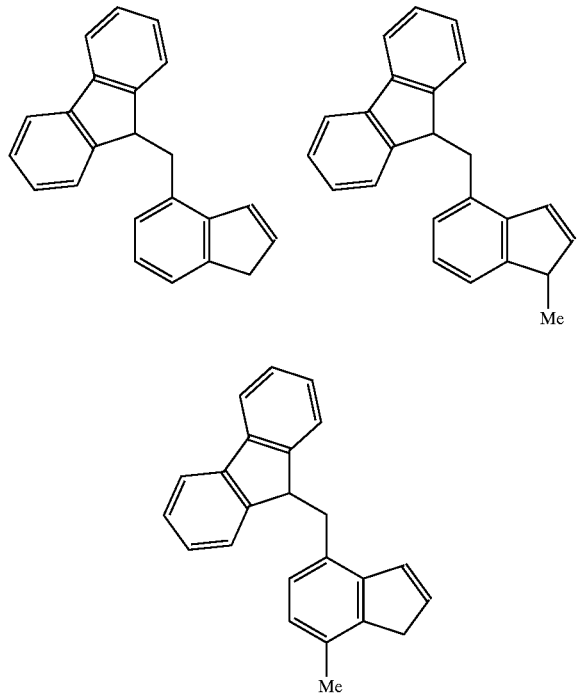

(I)

The compounds having general formula (Ia) can be prepared by means of a simple and original process which is illustrated in Scheme 1 below.

a =LiBu($_2$eq.)/hexane; b=diethylcarbonate; c= PTSA/toluene; d=LiAlH$_4$ or LiR or RMgX; e=PBr; f= Li(C$_5$HR$_3$R$_4$R$_5$R$_6$)

In particular said process comprises the following steps:

(a) reaction of 1-indanol derivatives having formula (II), wherein the R$_1$ and R$_2$ groups have the meaning defined above, with LiBu to give the double salt having formula (III);

(b) reaction of the double lithium salt having for-is mula (III), obtained in step (a), with electrophilic reagents, as diethyl carbonate, to obtain hydroxy ester (IV);

(c) dehydration reaction of the alcohol function of the hydroxyester having formula (IV), obtained in step (b), carried out in an acid environment to give the ester (V);

(d) reduction reaction of the ester having formula (v), obtained in step (c), to obtain the alcohol (VI);

(e) bromination reaction of the alcohol having formula (VI) to give the bromine derivative (VII);

(f) formation reaction of the indenyl derivative having formula (Ia), starting from the bromine derivative having formula (VII) obtained in step (e) and from lithium salts of cyclopentadienyl anions, whose corresponding neutral derivative can be represented by the following general formula (VIII):

Scheme 1

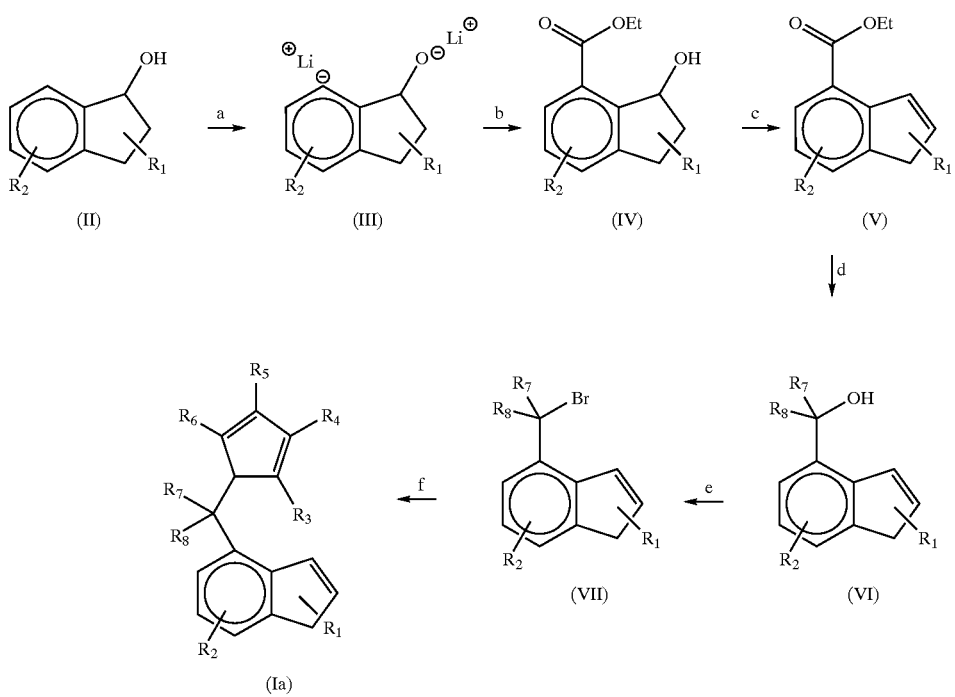

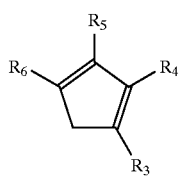

(VIII)

wherein each substituent $R_3$, $R_4$, $R_5$ and $R_6$ has the meanings defined above.

Step (a) of the process of the present invention described in Chem. Ber. (1980) 113, 1304.

In particular, this article discloses that some benzyl alcohols and other phenyl carbinols, among which 1-indanol (Synthesis (1981) 59) can be deprotonated in the presence of LiBu/tetramethylenediamine in pentane to give lithium (ortho-lithium)alkoxides.

The reaction described in step (a) can be carried out in the presence of base reagents such as, for example, lithium butyl, lithium methyl, sodium hydride in hydrocarbon and/ or ether solvents or their mixtures at temperatures ranging from −30° to 120° C.; the preferred conditions comprise the use of lithium butyl in hexane at temperatures ranging from 0° to 70° C.

Typical 1-indanols having general formula (II) are 1-indanol, 2-methyl-1-indanol, 3-methyl-1-indanol, 3-ethyl-1-indanol, 4-methyl-1-indanol.

One of the advantages of the process of the present invention consists in the fact that many 1-indanol derivatives are available on the market or can be easily prepared by means of well-known acylation/alkylation reactions of aromatic rings suitably substituted.

Step (b) of the process of the present invention comprises the reaction of the double lithium salt, having general formula (III), with electrophilic reagents among which diethyl carbonate, dimethyl carbonate, carbon dioxide, ethyl chloroformiate, are particularly appropriate for the purpose, in hydrocarbon and/or ether solvents or their mixtures at temperatures ranging from −100° to 120° C., preferably with diethyl carbonate in hexane at temperatures ranging from −70° to 25° C.

Step (c) of the process of the present invention consists in the dehydration of the hydroxy ester (IV) to obtain the corresponding indenyl derivative having general formula (V).

This reaction can be carried out in the presence of strong acids such as HCl, $H_2SO_4$, paratoluenesulfonic acid or blander dehydrating agents such as, for example, silica gel.

The choice of solvent for this reaction is very wide as it is possible to successfully use apolar solvents such as aliphatic hydrocarbons, medium polar solvents such as aromatic hydrocarbons or polar solvents such as ethers or chlorinated hydrocarbons; the temperature at which the reaction can take place can also be selected within a very wide range, typically from 25° to 150° C. and the selection generally depends not only on the substrate, but also on the type of solvent used, preferably paratoluenesulfonic acid in toluene is used at temperatures ranging from 50° to 110° C.

Step (d) of the process of the present invention comprises the reduction of the ester group to alcohol with the formation of the compound having general formula (VI); this reduction can be carried out with various reagents among which $LiAlH_4$, $NaBH_4$, NaH, $MgH_2$, LiBu, LiMe, MeMgCl, PhMgBr, Bu$^t$MgCl, generally in ether solvents, but it is also possible to use alternative solvents having other characteristics, at temperatures ranging from −70° to 100° C.; $LiAl_4$ in ethyl ether is preferably used at temperatures ranging from −30° to 25° C.

Step (e) of the process of the present invention comprises the bromination of the alcohol function to give the bromine derivative having general formula (VII); also in this case there are various synthetic alternatives, well known to experts in the field, which comprise the use of various brominating agents in different solvents; the preferred conditions comprise the use of $PBr_3$ in methylene chloride at temperatures ranging from −20° to 25° C.

Step (f) of the process of the present invention, comprises the reaction of a cyclopentadienyl anion with the bromine derivative having general formula (VII), obtained by the reaction of the corresponding neutral derivative, having general formula (VIII), with a suitable base.

Experts in the field know that there is a wide variety of products capable of satisfying this requirement; it is in fact possible to use alkyls or hydrides of electro-positive metals such as, for example, lithium methyl, lithium butyl, lithium ter-butyl, magnesium dibutyl, sodium hydride, potassium hydride, magnesium hydride, the well-known Grignard reagents: RMgX, or also the alkaline or earth-alkaline metals themselves or their alloys.

All the reagents are generally easy to find on the market, with acceptable costs, and consequently their selection frequently depends on the type of substrate whose anion is to be obtained.

The solvents for effecting this reaction can be selected from aliphatic or aromatic hydrocarbons, ethers and/or their mixtures, the preference of one or the other often depending on the particular demands of solubility or reaction rate of the case in question.

The temperatures at which the reaction is carried out can vary within a very wide range, typically from −80° to 110° C. and essentially depend on the thermal stability of the substrates and on the solvent used.

The preferred conditions for obtaining the anions of the compound having general formula (VIII) comprise the use of lithium butyl in mixtures of hexane/THF at temperatures ranging from 0° to 60° C.

Typical compounds having general formula (VIII) are: cyclopentadiene, methyl-cyclopentadiene, tetramethyl-cyclopentadiene, trimethylsilyl-cyclopentadiene, indene, 3-meth-yl-indene, 4,7-dimethyl-indene, 5,6dimethyl-indene, 4,5,6,7-tetrahydro-indene, 4,5,6,710 tetrahydro-2-methyl-ind-ene, 2,4,5,6,7,8-hexahydro-azulene, 2-methyl-2,4,5,6,7,8-hexahydro-azulene, 4,5,6,7,8,9-hexahydro-2H-cyclopentacyc-lo-octene, 4,5,6,7,8,9,10,11,12,13-decahydro-2H-cyclopen-tacyclododecene, fluorene, 1,2,3,4,5,6,7,8-octa-hydro-fluo-rene.

In the preferred embodiment, the compound having general formula (VIII) is cyclopentadiene, tetramethyl-cyclopentadiene, indene, 3-methyl-indene, 4,7dimethyl-indene, 2,4,5,6,7,8-hexahydro-azulene, fluo-rene.

In an even more preferred embodiment the compound having general formula (VIII) is indene, 4,7-dimethyl-indene.

This reaction can be carried out in a wide variety of solvents selected from aromatic and/or aliphatic phatic hydrocarbons and from ethers and/or their mixtures, at a temperature ranging from −80° to 120° C. There are no particular limitations in the order of addition of the various reagents, but it is preferable to operate by adding the bromine derivative (VII), either pure or diluted in ether solvent, to the solution/suspension containing the cyclopentadienyl anion, obtained as described above, at temperatures ranging from −70° to 25° C.

Alternatively, step (f) of the process of the present invention can be carried out by reacting the brominated product (VII) with a suitable lithium enolate giving rise to the formation of indenyl-cyclopentadienyl products having general formula (XIII):

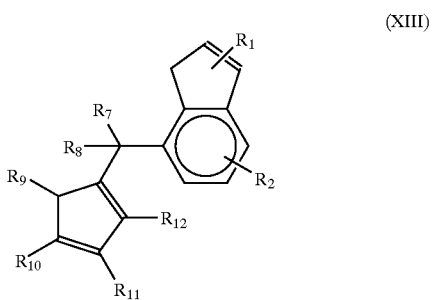

wherein:

$R_1$ and $R_2$ can independently occupy any of the free positions of the indene group;

$R_1$, $R_2$, $R_7$, $R_8$, $R_9$, $R_{10}$ and $R_{11}$ independently represent hydrogen, halogen, preferably F, Cl or Br, a linear or branched $C_1$–$C_{20}$ hydrocarbyl group, saturated or unsaturated, cycloaliphatic or aromatic, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements, preferably Si, O, N, S, P, or, wherein any two of the substituents $R_9$, $R_{10}$ and $R_{11}$, adjacent to each other, are joined to each other to form a saturated or unsaturated $C_4$–$C_{20}$ cyclic structure, comprising a bond of the cyclopentadienyl ring, said structure optionally containing one or more of the heteroatoms specified above;

$R_{12}$ can be independently hydrogen, a linear or branched $C_1$–$C_{20}$ hydrocarbyl group, saturated or unsaturated, cycloaliphatic or aromatic, or a $C_1$–$C_{20}$ hydrocarbyl group comprising one or more heteroatoms of groups 14 to 16 of the periodic table of elements, preferably Si, O, N, S, P.

The variant in step (f) of the process of the present invention is indicated in Scheme 2:

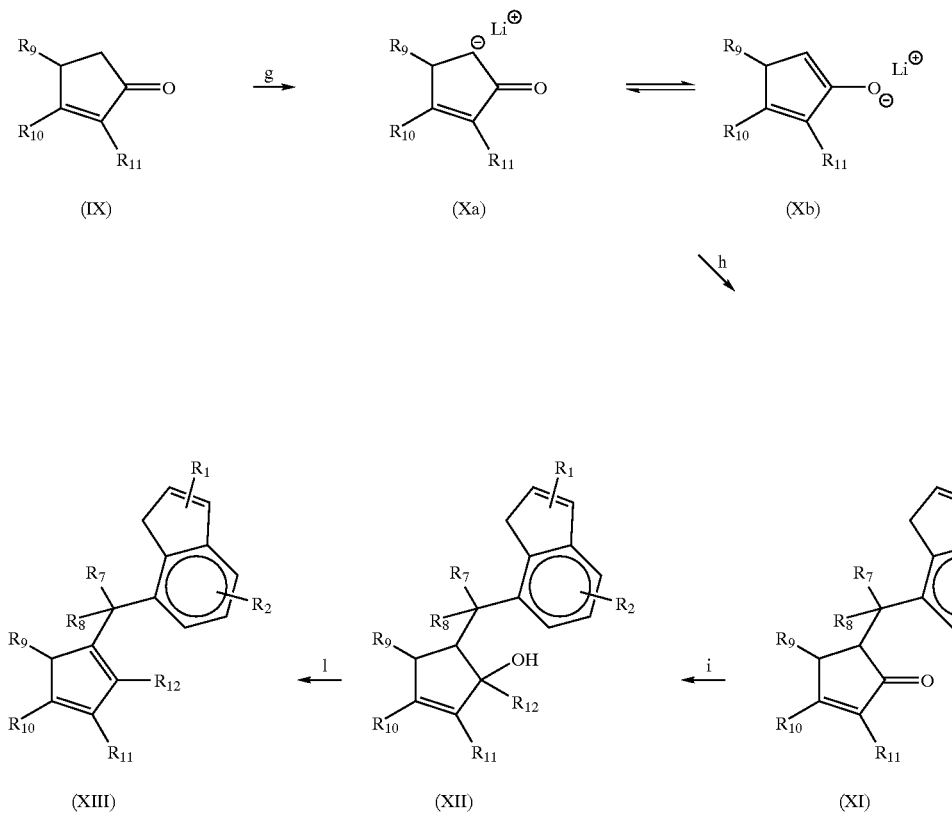

g:Li[N(iso-Pr)$_2$]/THF/−78° C, h: (VII)/THF;i:NaBH$_4$ or LiR$_{12}$ or R$_{12}$MgX; 1: CuSO$_4$/toluene/110° C.

In accordance with this, a further object of the present invention relates to a variant of the process for the preparation of compounds having general formula (Ia), which gives rise to the formation of analogous products having general formula (XIII) wherein the substituents R$_1$, R$_2$, R$_7$, R$_8$, R$_9$, R$_{10}$, R$_{11}$ and R$_{12}$ have the meaning defined above, which comprises the following steps:

(g) reaction of a cyclic ketone, having general formula (IX), wherein the groups R$_9$, R$_{10}$ and R$_{11}$, have the meaning defined above, with a lithium amide to give the mixture of anions having general formula (Xa)/(Xb);

(h) reaction of the mixture of anions (Xa)/(Xb) with the brominated product having general formula (VII), prepared according to what is indicated above (Scheme 1);

(i) reduction of the functional carbonyl group to alcohol, by means of suitable reagents, with the formation of the derivative having general formula (XII), wherein the R$_{12}$ group has the meaning defined above;

(1) dehydration of the derivative having general formula (XII), obtained in step (i), with the formation of the desired indenyl-cyclopentadienyl compound, having general formula (XIII), wherein the groups R$_1$, R$_2$, R$_7$, R$_8$, R$_9$, R$_{10}$, R$_{11}$ and R$_{12}$ have the meaning defined above.

In step (g) a cyclic ketone having general formula (IX) is reacted with a strong non-alkylating base, in ether solvents such as ethyl ether, tetrahydrofuran, dioxane, as the dissolving capacity of the latter can improve the reaction kinetics, but this does not mean that less polar solvents, such as aromatic and/or aliphatic hydrocarbons, can also be conveniently used for the purpose, at temperatures ranging from −80° C. to 110° C., the selection of the latter depending on the type of solvent and substrates used.

Typical strong bases, suitable for the purpose, are alcoholates of alkaline and earth-alkaline metals such as for example lithium methoxide, sodium methoxide, sodium ethoxide, sodium iso-propoxide, potassium ter-butoxide, magnesium di-ethoxide, etc. or the relative amides such as, for example, lithium amide, sodium amide, lithium di-ethylamide, lithium diisopropylamide, lithium bis-(trimethylsilyl)amide, potassium di-butylamide, etc.

In the preferred embodiment the strong bases are selected from lithium methoxide, sodium ethoxide, potassium ter-butoxide, sodium amide, lithium diisopropylamide.

In an even more preferred embodiment the strong base is lithium di-isopropylamide.

Typical cyclic ketones having general formula (IX), suitable for being used in step (g) of Scheme 2 are: cyclopent-1-en-3-one, 1-methyl-cyclopent-1-en-3-one, 1,2,5-tri-methyl-cyclopent-1-en-3-one, indan-1-one, 3-methyl-indan-1-one, 4,7-dimethyl-indan-1-one, indan-2-one, etc.

In the preferred embodiment the cyclo-ketone compound having general formula (IX) is selected from cyclopent-1-en-3-one, 1,2,5-trimethylcyclopent-1-en-3-one, indan-1-one, 3-methyl-indan-1-one; in an even more preferred embodiment compound (IX) is indan-lone.

Step (h) of the process of the present invention consists in the reaction between the mixture of anions (Xa)/(Xb) with the brominated product (VII), prepared according to Scheme 1, which can be carried out in hydrocarbon, ether solvents or their mixtures, the use of the same solvent adopted in the previous step (g), normally being preferred, at temperatures ranging from −80° C. to 70° C.

In a preferred embodiment, the reaction is carried out in a mixture of THF/hexane at temperatures ranging from −70° to 25° C.

Step (i) of the process of the present invention consists in a reduction of the functional carbonyl group, present in the derivative having general formula (XI), to alcohol, with the formation of the compound having general formula (XII). There are various possibilities, well known to experts in the field, for selecting the reducing reagents suitable for the purpose, among which lithium aluminum hydride, sodium boron hydride, sodium hydride, lithium methyl, lithium phenyl, ethyl magnesium bromide, isopropyl magnesium bromide, etc., which can be successfully used either in hydrocarbon or ether solvents or their mixtures, at temperatures ranging from −40° to 70° C. In a preferred embodiment, sodium boron hydride in tetrahydrofuran is used at temperatures ranging from −20° to 25° C.

Step (1) of the process of the present invention, consists in the dehydration of the derivative (XII), obtained in step (i), to give the desired indenyl-cyclopentadienyl product having general formula (XIII).

The latter can be carried out in the presence of dehydrating agents such as, for example, silica gel, strong acids such as HCl, H$_2$SO$_4$, paratoluenesulfonic acid, or anhydrous inorganic salts such as, for example, Cu (SO$_4$), Mg(SO$_4$), Na(SO$_4$)$_2$, CaCl$_2$, etc.

The selection of the solvent for this reaction is very wide as it is possible to successfully use apolar solvents such as aliphatic hydrocarbons, medium polar solvents such as aromatic hydrocarbons or polar solvents such as ethers or chlorinated hydrocarbons; the temperature at which the reaction takes place can also be selected within a very wide range, typically from—20° to 130° C. and the selection generally depends not only on the substrate but also on the type of solvent used. In a preferred embodiment anhydrous Cu (SO$_4$) is used in toluene at 110° C.

The processes of the present invention do not necessarily require the isolation of the single reaction products at the end of the respective steps.

In addition to the advantage of starting from products which are easily available, the processes comprise quite simple chemical passages and produce satisfactory overall yields.

The preparation of the complexes having general formula (I) can be carried out according to one of the well-known methods described in literature for the production of bridged bis-cyclopentadienyl complexes of transition metals.

The method most commonly used comprises reacting a salt of the metal M (preferably a chloride), with a salt of an alkaline metal of the dianion of the bis-cyclo-pentadienyl ligand having the desired structure.

The preparation of the complexes having formula (I) normally comprises two steps, in the first of which the ligand having general formula (Ia) is reacted with a lithium alkyl, such as lithium methyl or lithium butyl, in an inert solvent, preferably consisting of an aromatic hydrocarbon or an ether, particularly tetrahydrofuran or ethyl ether.

The temperature during the reaction is preferably maintained below room temperature to avoid the creation of secondary reactions. At the end of the reaction the corresponding lithium salt of the cyclopentadienyl dianion is obtained.

In the second step, the salt of the cyclopentadienyl dianion is reacted with a salt, preferably a chloride, of the transition metal M, again in an inert organic solvent at a temperature preferably ranging from −30° to 70° C.

At the end of the reaction, the complex having formula (I) thus obtained is separated and purified according to the known methods of organometallic chemistry.

As is known to experts in the field, the above operations are sensitive to the presence of air and humidity and should therefore be carried out in an inert atmosphere, preferably under nitrogen or argon.

Numerous general and specific methods which substantially originate from the method indicated above, are described in literature, such as, for example in the publications of D. J. Cardin "Chemistry of Organo Zr and Hf Compounds" J. Wiley and Sons Ed., New York (1986); R. Haltermann "Chemical Review", vol. 92 (1992) pages 965–994; R. O. Duthaler and A. Hafner "Chemical Review", vol. 92 (1992) pages 807–832.

The metallocene compounds of the present invention can be conveniently used as catalytic components for the polymerization of olefins.

A further object of the present invention therefore relates to a catalyst for the polymerization of olefins comprising the reaction product between:

(A) a metallocene compound having formula (I) obtained as described above, and
(B) one or more compounds capable of activating the metallocene (I) selected from those known in the art, particularly an organic derivative of an element M' different from carbon and selected from the elements of groups 1, 2, 12, 13 and 14 of the periodic table.

In particular, according to the present invention, said element M' is selected from boron, aluminum, zinc, magnesium, gallium and tin, more particularly boron and aluminum.

In a preferred embodiment of the present invention, the component (B) is an organo-oxygenated derivative of aluminum, gallium or tin. This can be defined as an organic compound of M', in which the latter is bound to at least one oxygen atom and to at least one organic group consisting of an alkyl group having from 1 to 12 carbon atoms, preferably methyl.

According to this aspect of the invention, component (B) is more preferably an aluminoxane. As is known, aluminoxanes are compounds containing Al—O—Al bonds, with a varying O/Al ratio, which can be obtained, under controlled conditions, by the reaction of an aluminum alkyl or aluminum alkyl halide, with water or other compounds containing pre-established quantities of water available, such as, for example, in the case of the reaction of aluminum trimethyl with aluminum sulfate hexahydrate, copper sulfate pentahydrate or iron sulfate pentahydrate.

Aluminoxanes preferably used for the formation of the polymerization catalyst of the present invention are oligo-poly-meric, cyclic and/or linear compounds, characterized by the presence of repetitive units having the following formula:

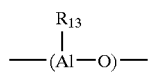

wherein $R_{13}$ is a $C_1$–$C_{12}$ alkyl group, preferably methyl.

Each dialuminoxane molecule preferably contains from 4 to 70 repetitive units which may also not all be equal to each other, but contain different $R_{13}$ groups.

When used for the formation of a polymerization catalyst according to the present invention, the aluminoxanes are put in contact with a complex having formula (I) in such proportions that the atomic ratio between Al and the transition metal M is within the range of 10 to 10000 and preferably from 100 to 5000. The sequence with which the complex (I) and the aluminoxane are put in contact with each other, is not particularly critical.

In addition to the above aluminoxanes, the definition of component (B) according to the present invention also comprises galloxanes (in which, in the previous formulae, gallium is present instead of aluminum) and stannoxanes, whose use as cocatalysts for the polymerization of olefins in the presence of metallocene complexes is known, for example, from patents U.S. Pat. No. 5,128,295 and U.S. Pat. No. 5,258,475.

According to another preferred aspect of the present invention, said catalyst can be obtained by putting component (A) consisting of at least on complex having formula (I), in contact with component (B) consisting of at least one compound or a mixture of organometallic compounds of M' capable of reacting with the complex having formula (I), extracting from this a σ-bound group R' to form, on the one hand at least one neutral compound, and on the other hand an ionic compound consisting of a metallocene cation containing the metal M and an organic non-coordinating anion containing the metal M', whose negative charge is delocalized on a multicenter structure.

Components (B) suitable as ionizing systems of the above type are preferably selected from the voluminous organic compounds of boron and aluminum, such as for example, those represented by the following general formulae:

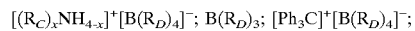
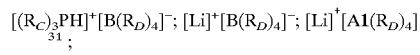

wherein the deponent "x" is an integer ranging from 0 to 3, each $R_c$ group independently represents an alkyl or aryl radical having from 1 to 12 carbon atoms and each RD group independently represents an aryl radical partially or, preferably, totally fluorinated, having from 6 to 20 carbon atoms.

Said compounds are generally used in such quantities that the ratio between the atom M' of component (B) and the atom M of component (A) is within the range of 0.1 to 15, preferably from 0.5 to 10, more preferably from 1 to 6.

Component (B) can consist of a single compound, normally an ionic compound, or a combination of this compound with MAO, or, preferably, with an aluminum trialkyl having from 1 to 16 carbon atoms in each alkyl residue, such as for example $ALMe_3$, $AlEt_3$, $Al(i\text{-}Bu)_3$.

In general, the formation of the ionic metallocene catalyst, in accordance with the present invention, is preferably carried out in an inert liquid medium, more preferably hydrocarbon. The selection of components (A) and (B) which are preferably combined with each other, as well as the particular method used, can vary depending on the molecular structures and result desired, according to what is described in detail in specific literature available to experts in the field.

Examples of these methods are qualitatively schematized in the list provided hereunder, which however does not limit the overall scope of the present invention:

(i) by contact of a metallocene having general formula (I) wherein at least one, preferably both, of the substituents $X_1$ and $X_2$ is hydrogen or an alkyl radical, with an ionic compound whose cation is capable of reacting with one of the substituents $X_1$ or $X_2$ to form a neutral compound, and whose anion is voluminous, non-coordinating and capable of delocalizing the negative charge;

(ii) by the reaction of a metallocene having the previous formula (I) with an alkylating agent, preferably an aluminum trialkyl, used in molar excess of 10/1 to 500/1, followed by the reaction of a strong Lewis acid, such as for example, tris(pentafluo-rophenyl)boron a in more or less stoichiometric quantity or in slight excess with respect to the metal M;

(iii) by contact and reaction of a metallocene having the previous formula (I) with a molar excess of 10/1 to 1000/1, preferably from 30/1 to 500/1 of an aluminum trialkyl or an alkylaluminum halide or one of their mixtures, which can be represented by the formula $AlR_mX_{3-m}$, wherein R is a linear or branched $C_1$–$C_{12}$ alkyl group, X is a halogen, preferably chlorine or bromine, and "m" is a decimal number ranging from 1 to 3; followed by the addition to the composition thus obtained, of at least an ionic compound of the type described above in such quantities that the ratio between B or Al and the atom M in the metallocene complex is within the range of 0.1 to 20, preferably from 1 to 6.

Examples of ionizing ionic compounds or multicomponent reactive systems capable of producing an ionic catalytic system by reaction with a metallocene complex, according to the present invention, are described in the following patent publications, whose content in herein incorporated as reference:

European patent application, published under the Nr.: EP-A 277,003, EP-A 277,004, EP-A 522,581, EP-A 495,375, EP-A 520,732, EP-A 478,913, EP-A 468,651, EP-A 427,697, EP-A 421,659, EP-A 418,044;

International patent applications published under the Nr.: WO 92/00333, WO 92/05208; WO 91/09882;

Patents U.S. Pat. No. 5,064,802, U.S. Pat. No. 2,827,446, U.S. Pat. No. 5,066,739.

Also included in the scope of the present invention are those catalysts comprising two or more complexes having formula (I) mixed with each other. Catalysts of the present invention based on mixtures of complexes having different catalytic activities can be advantageously used in polymerization when a wider molecular weight distribution of the polyolefins thus produced is desired.

According to an aspect of the present invention, in order to produce solid components for the formation of catalysts for the polymerization of olefins, the above complexes can also be supported on inert solids, preferably consisting of oxides of Si and/or Al, such as for example, silica, alumina or silica-aluminates.

For the supporting of said catalysts, the known supporting techniques can be used, normally comprising contact, in a suitable inert liquid medium, between the carrier, optionally activated by heating to temperatures exceeding 200° C., and one or both of components (A) and (B) of the catalyst of the present invention. For the purposes of the present invention, it is not necessary for both components to be supported, as it is also possible for only the complex having formula (I) or the organic compound of B, Al, Ga or Sn as defined above, to be present on the surface of the carrier. In the latter case, the component which is not present on the surface is subsequently put in contact with the supported component, at the moment of the formation of the catalyst active for the polymerization.

Also included in the scope of the present invention are the complexes, and catalytic systems based on these, which have been supported on a solid by means of the functionalization of the latter and formation of a covalent bond between the solid and a metallocene complex included in formula (I) above.

A particular method for the formation of a supported catalyst according to the present invention comprises prepolymerizing a relatively small fraction of monomer or mixture of monomers in the presence of the catalyst, so as to include this in a solid microparticulate, which is then fed to the actual reactor itself for completing the process in the presence of an additional olefin(s). This provides a better control of the morphology and dimensions of the polymeric particulate obtained at the end.

One or more other additives or components can be optionally added to the catalyst according to the present invention, as well as the two components (A) and (B), to obtain a catalytic system suitable for satisfying specific requisites. The catalytic systems thus obtained should be considered as being included in the scope of the present invention. Additives or components which can be included in the preparation and/or formulation of the catalyst of the present invention are inert solvents such as, for example, aliphatic and/or aromatic hydrocarbons, aliphatic and aromatic ethers, weakly co-ordinating additives (Lewis bases) selected, for example, from non-polymerizable olefins, ethers, tertiary amines and alcohols, halogenating agents such as silicon halides, halogenated hydrocarbons, preferably chlorinated, and the like, and again all other possible components normally used in the art for the preparation of the traditional homogeneous catalysts of the metallocene type for the (co)polymerization of olefins.

Components (A) and (B) form the catalyst of the present invention by contact with each other, preferably at temperatures ranging from 20° to 60° C. and for times varying from 10 seconds to 1 hour, more preferably from 30 seconds to 15 minutes.

The catalysts according to the present invention can be used with excellent results in substantially all known (co) polymerization processes of olefins, either in continuous or batchwise, in one or more steps, such as, for example, processes at low (0.1–1.0 MPa), medium (1.0–10 MPa) or high (10–150 MPa) pressure, at temperatures ranging from 10° to 240° C., optionally in the presence of an inert diluent. Hydrogen can be conveniently used as molecular weight regulator.

These processes can be carried out in solution or suspension in a liquid diluent normally consisting of an aliphatic or cycloaliphatic saturated hydrocarbon, having from 3 to 20 carbon atoms or a mixture of two or more of these, but which can also consist of a monomer as, for example, in the known co-polymerization polymerization process of ethylene and propylene in liquid propylene. The quantity of catalyst introduced into the polymerization mixture is preferably selected so that the concentration of the metal M ranges from $10^{-4}$ to $10^{-8}$ moles/liter.

Alternatively, the polymerization can be carried out in gas phase, for example, in a fluid bed reactor, normally at pressures ranging from 0.5 to 5 MPa and at temperatures ranging from 50 to 150° C.

According to a particular aspect of the present invention, the catalyst for the (co)polymerization of ethylene with other olefins is prepared separately (preformed) by contact of components (A) and (B), and is subsequently introduced into the polymerization environment.

The catalyst can be first charged into the polymerization reactor, followed by the reagent mixture containing the olefin or mixture of olefins to be polymerized, or the catalyst can be charged into the reactor already containing the reagent mixture, or finally, the reagent mixture and the catalyst can be contemporaneously fed into the reactor.

According to another aspect of the present invention, the catalyst is formed "in situ", for example by introducing components (A) and (B) separately into the polymerization reactor containing the pre-selected olefinic monomers.

The catalysts according to the present invention can be used with excellent results in the polymerization of ethylene to give linear polyethylene and in the copolymerization of ethylene with propylene or higher olefins, preferably having from 4 to 12 carbon atoms, to give copolymers having different characteristics depending on the specific polymerization conditions and on the quantity and structure of the comonomer used.

For example, linear polyethylenes can be obtained, with a density ranging from 0.880 to 0.940, and with molecular weights ranging from 10,000 to 2,000,000. The olefins preferably used as comonomers of ethylene in the production of low or medium density linear polyethylene (known with the abbreviations ULDPE, VLDPE and LLDPE depending on the density), are 1-butene, 1-hexene and 1-octene.

The catalyst of the present invention can also be conveniently used in copolymerization processes of ethylene and propylene to give saturated elastomeric copolymers vulcanizable by means of peroxides and extremely resistant to aging and degradation, or in the terpolymerization of ethylene, propylene and a diene, generally non-conjugated, having from 4 to 20 carbon atoms, to obtain vulcanizable rubbers of the EPDM type.

In the case of these latter processes, it has been found that the catalysts of the present invention allow the production of polymers having a particularly high comonomer content and average molecular weight under the polymerization conditions.

In the case of the preparation of EPDM, the dienes which can be used for the purpose are preferably selected from:
- linear chain dienes such as 1,4-hexadiene and 1,6-octadiene;
- branched dienes such as 5-methyl-1,4-hexadiene; 3,7-dimethyl-1,6-octadiene; 3,7-dimethyl-1,7-octadiene;
- dienes with a single ring such as 1,4cyclohexadiene; 1,5-cyclo-octadiene; 1,5-cyclododecadiene;
- dienes having bridged condensed rings such as dicyclopentadiene; bicyclo[2.2.1]hepta-2,5-diene; alchenyl, alkylidene, cycloalkenyl and cycloalky-lidene norbornenes such as 5-methylene-2norbornene, 5-ethylidene-2-borbornene (ENB), 5-propenyl-2-norbornene.

Among the non-conjugated dienes typically used for preparing these copolymers, dienes containing at least one double bond in a stretched ring are preferred, even more preferably 5-ethylidene-2-norbornene (ENB), and also 1,4-hexadiene and 1,6-octadiene.

In the case of EPDM terpolymers, it is convenient for the quantity of dienic monomer not to exceed 15% by weight, and it is preferably from 2 to 10% by weight. The propylene content on the other hand ranges from 20 to 55% by weight.

The catalysts of the present invention can also be used in homo- and co-polymerization processes of olefins according to the known techniques, giving, with excellent yields, atactic, isotactic or syndiotactic polymers, depending on the structure and geometry of the metallocene complex having formula (I).

Olefins suitable for the purpose are those having from 3 to 20 carbon atoms, optionally also comprising halogens and/or other heteroatoms or aromatic nuclei such as, for example, propylene, 1-butene, 1-hexene, 1-octene, 4-methyl-1-pentene, 1-decene and styrene.

The present invention is further described by the following examples, which, however, are provided for purely illustrative purposes and do not limit the overall scope of the invention itself.

Characterization Methods

The analytical techniques and characterization methods used in the examples are listed below and are briefly described.

The characterization by means of NMR spectroscopy mentioned in the following examples was carried out on a nuclear magnetic resonance spectrometer mod. Bruker MSL-300, using, unless otherwise specified, $CDCl^3$ as solvent for each sample.

The molecular weight measurement of the olefinic polymers was carried out by means of Gel-Permeation Chromatography (GPC). The analyses of the samples were effected in 1,2,4-trichlorobenzene (stabilized with Santonox) at 135° C. with a WATERS 150-CV chromatograph using a Waters differential refractometer as detector. The chromatographic separation was obtained with a set of $\mu$-Styragel HT columns (Waters) of which three with pore dimensions of $10^3$, $10^4$, $10^5$ Å respectively, and two with pore dimensions of $10^6$ Å, establishing a flow-rate of the eluant of 1 ml/min. The data were obtained and processed by means of Maxima 820 software version 3.30 (Millipore); the number $(M_n)$ and weight $(M_w)$ average molecular weight calculation was carried out by universal calibration, selecting polystyrene standards with molecular weights within the range of 6,500,000–2,000, for the calibration.

The determination of the content of units deriving from propylene and possible diene in the polymers is carried out (according to the method of the Applicant) by means of IR on the same polymers in the form of films having a thickness of 0.2 mm, using an FTIR Perkin-Elmer spectrophotometer model 1760. The intensity of the characteristic peaks is measured, of propylene at 4390 cm$^{-1}$ and ENB at 1688 cm$^{-1}$ respectively, in relation to the peak at 4255 cm$^{-1}$, and the quantity is determined using a standard calibration curve.

The Melt Flow Index (MFI) of the polymers is determined in accordance with the regulation ASTM D-1238 D.

The Mooney viscosity (1+4) is determined at 100° C. using a Monsanto "1500 S" viscometer according to the method ASTM D 1646/68.

EXAMPLE 1

Synthesis of
1-methyl-4-methylene(1-indenyl)indene

The following products are reacted:
170 ml of benzene
22.7 g (264 mmoles) of crotonic acid
106 g (795.2 mmoles) of aluminum trichloride

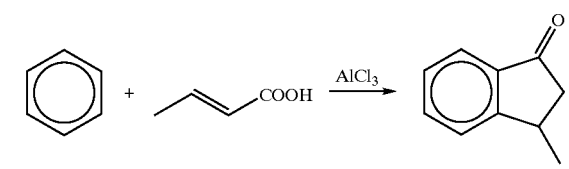

The solution of crotonic acid in 100 ml of benzene is added dropwise to the suspension of AlCl$_3$ in 70 ml of benzene. The mixture is stirred at 80° C. for 5 hours. It is poured into ice and is extracted with ethyl ether. After washing until neutrality with a saturated aqueous solution of NaHCO$_3$ and water and anhydrifying on Na$_2$SO$_4$, the solvent is evaporated. The product is purified by distillation (T$_{boil.}$=125° C.). 32.0 g are obtained (yield=83%).

32.0 g (219.2 mmoles) of 3-methyl-1-indanone, obtained in the previous step, are reacted with:

5.6 g (147 mmoles) of sodium boronhydride
128 ml of tetrahydrofuran
64 ml of methanol

NaBH$_4$ is added, in portions, to the solution of 3methyl-1-indanone in tetrahydrofuran and methanol, at 0° C. After 2 hours the mixture is poured into ice and is extracted with ethyl ether. After washing the organic extracts to neutrality with a saturated solution of NaCl and anhydrifying on Na$_2$SO$_4$, the mixture is filtered and the solvent evaporated. 30.8 g of product are obtained (95%).

14.8 g (0.1 moles) of 3-methyl-1-indanol, obtained in the previous step, are reacted with:

80 ml (0.2 moles) of LiBu 2.5 M in hexane
26.7 ml (0.22 moles) of diethylcarbonate
500 ml of hexane

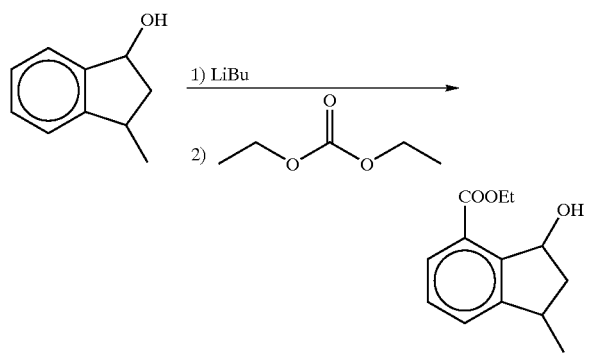

N-butyl lithium is added, by means of a drip funnel, over a period of about 1 h, in an inert atmosphere, to the suspension of 3-methyl-1-indanol in hexane, at 20° C. At the end of the addition the reaction mixture is heated to 60° C. for 2 h, and, after cooling to −70° C., diethyl carbonate is then added. The temperature is left to rise slowly to 25° C. and, after a further 8 h, the reaction mass is poured into water and is extracted with ethyl ether. The separated organic phase is washed with water until neutrality, anhydrified on sodium sulfate and the solvent is evaporated at reduced pressure. After purification on a silica gel column (eluant: hexane/ethyl acetate 9/1), 5.6 g of 3-methyl-7-carboethoxy-1-indanol are obtained.

5.6 g (25.45 mmoles) of 3-methyl-7-carboethoxy-1-indanol
80 ml of toluene
0.1 g (0.58 mmoles) of p-toluenesulfonic acid (PTSA)

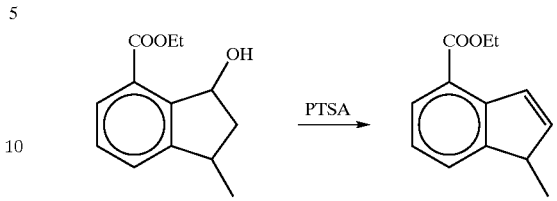

Para-toluenesulfonic acid is added to the solution of 3-methyl-7-carboethoxy-1-indanol in toluene. The mixture is heated to 100° C. and the water is removed by azeotropic distillation. After 2 h a saturated aqueous solution of NaHCO$_3$ is added, the organic phase is separated, washed with water until neutrality and anhydrified on NaSO$_4$. Finally the solvent is removed at reduced pressure and, after purification on a silica gel column (eluant: hexane/ethyl acetate 95/5), 5.0 g of 3-methyl-7-carboethoxy-1-indene are obtained.

5.0 g (24.7 mmoles) of 3-methyl-7-carboethoxy-1-indene
0.6 g (15.8 mmoles) of LiAlH$_4$
100 ml of ethyl ether

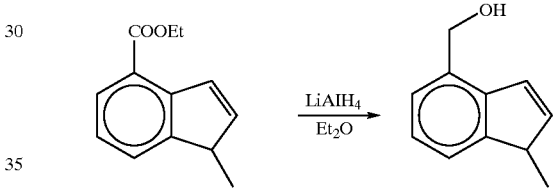

A solution of 3-methyl-7-carboethoxy-1-indene in 40 ml of ethyl ether are added, at −30° C., to the suspension of LiAlH$_4$ in 60 ml of ethyl ether. The temperature is slowly left to rise to 25° C. and after 30 min water is slowly added and the mixture is acidified with HCl 2M. The reaction mass is extracted with ethyl ether, washed repeatedly with water until neutrality and dried on NaSO$_4$. The solvent is finally removed under vacuum and 3.76 g of 7-(3-methylindenyl) methanol are obtained.

3.76 g (23.5 mmoles) of 7-(3-methylindenyl)methanol
2.1 g (7.86 mmoles) of PBr$_3$
50 ml of methylene chloride

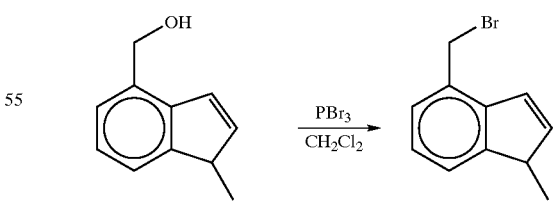

Phosphorous tribromide is slowly added, by means of a drip funnel, to the solution of 7-(3methylindenyl)methanol in CH$_2$Cl$_2$, cooled to −20° C. The temperature is left to rise to 25° C. and after 30 min a saturated aqueous solution of NaHCO$_3$ is slowly added. The reaction mass is extracted various times with ethyl ether, the organic extracts are washed with water until neutrality and dried on NaSO$_4$.

After removing the solvent at reduced pressure, 4.9 g of 4bromomethyl-1-methylindene are obtained.

7 g (31.4 mmoles) of 4-bromomethyl-1-methylindene, obtained in the previous step, are reacted with:
31 ml (77.5 mmoles) of LiBu 2.5 M in hexane
200 ml of THF
7.3 ml (62.3 mmoles) of indene

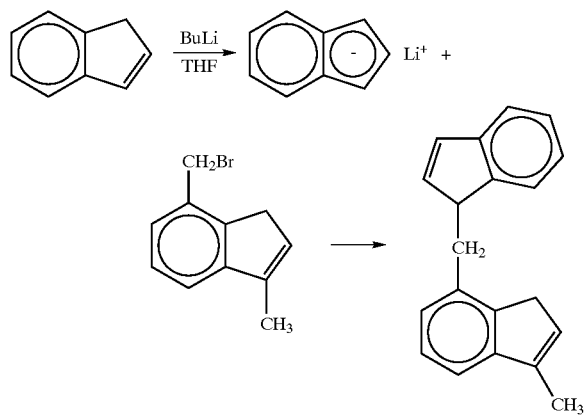

Butyl lithium is added dropwise to the solution of indene in 100 ml of THF. The mixture is left under stirring for 2 h at room temperature and is then cooled to −70° C. Bromine dissolved in THF is added. After 1 h at this temperature the mixture is left to rise to room temperature and is poured into water. It is extracted with ethyl ether, the extracts are washed until neutrality and are anhydrified on sodium sulfate. The residue obtained by evaporation of the solvent is purified on a silica gel column using petroleum ether as eluant. In this way 4.3 g of 1-methyl-4-methylene (1-indenyl)indene are obtained (53% yield).

EXAMPLE 2

Synthesis of 4-methylene(1-indenyl)indene

The following products are reacted:
16.0 g (119.4 mmoles) of 1-indanol
100 ml (250 mmoles) of LiBu 2.5 M in hexane
31.5 (259.6 mmoles) of diethylcarbonate
500 ml of hexane

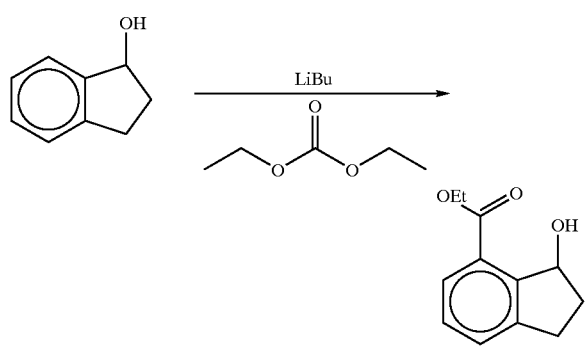

N-butyl-lithium is added dropwise to the suspension in 1-indanol in hexane, at −5° C. The mixture is stirred at 60° C. for 2 hours and diethylcarbonate is added, at −70° C. The mixture is left to rise to room temperature. After 8 hours, it is poured into water and extracted with ethyl ether. After washing the organic extracts to neutrality and anhydrifying on $Na_2SO_4$, the solvent is evaporated under vacuum. The product is purified by chromatographic separation on silica gel eluating with hexane and ethyl acetate in a ratio of 95/5. 6 g of product are obtained (yield=24.5%).

5 g (24.3 mmoles) of hydroxy-ester, obtained in the previous step, are reacted with:
200 mg (1.05 mmoles) of para-toluenesulfonic acid
20 ml of toluene

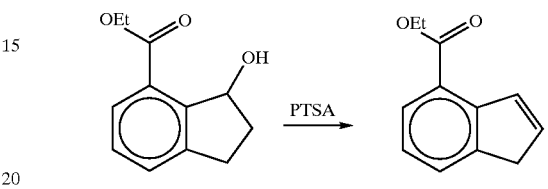

The toluene solution of hydroxy ester and PTSA are stirred at 90° C. for 3 hours. The mixture is washed, until neutrality, with a saturated aqueous solution of $NaHCO_3$ and with water. After anhydrifying the organic phase on $Na_2SO_4$ and filtering, the solvent is evaporated. The residue is purified on a silica gel chromatographic column with hexane and ethyl acetate as eluant in a ratio of 95/5. 4.0 g of ester are thus obtained (yield 87.7%).

8.8 g (46.8 mmoles) of ester, obtained in the previous step, are reacted with:
2.1 g (55.3 mmoles) of lithium aluminum hydride
120 ml of ethyl ether.

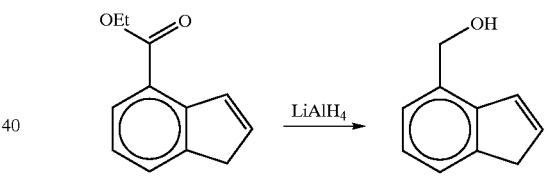

The ester dissolved in 20 ml of ethyl ether is added, at −20° C. to the suspension, in ethyl ether, of $LiAlH_4$. After 6 hours water is slowly added, the mixture is acidified with HCl (2N) and extracted with ethyl ether. After washing the organic extracts to neutrality and anhydrifying on $Na_2SO_4$, the mixture is filtered and the solvent evaporated. 6.6 g of alcohol are obtained (yield 96%).

6.6 g (45.2 mmoles) of alcohol, obtained in the previous step, are reacted with:
1.5 ml (15.82 mmoles) of phosphorous tribromide
70 ml of methylene chloride

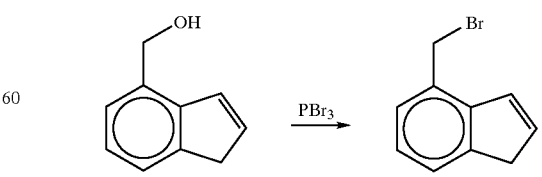

The phosphorous tribromide is added dropwise to the solution, in methylene chloride, of alcohol at −20° C. After 1 hour a saturated aqueous solution of $NaHCO_3$ is added dropwise and the mixture is extracted several times with ethyl ether. After washing the organic extracts to neutrality and anhydrifying on $Na_2SO_4$, the mixture is filtered and the solvent evaporated. 5.0 g of 4-bromomethyl-indene are obtained (yield 53%).

4.44 ml (33.6 mmoles) of indene
15 ml (33.6 mmoles) of LiBu solution 2.5 M in hexane
5 g (24 mmoles) of 4-bromomethyl-indene
90 ml of tetrahydrofuran
45 ml of hexane N-butyl-lithium is added, at 5° C, to the solution, in THF in hexane, of indene. After 1 hour, the mixture is cooled to −70° C. and benzyl bromide dissolved in 20 ml of THF is added. The mixture is left to rise to room temperature. After 8 hours, it is poured into water and is extracted with ethyl ether. After washing the ether extracts to neutrality with water and anhydrifying on $Na_2SO_4$, the mixture is filtered and the solvent evaporated.

After purification on a silica gel chromatographic column (eluant: hexane), 2.3 g of 4-methylene(1-indenyl) indene are obtained (yield 39.3%)

EXAMPLE 3

Synthesis of 7-methyl-4-methylene(4,7-dimethyl-1indenyl)-indene

The following reaction scheme is followed:

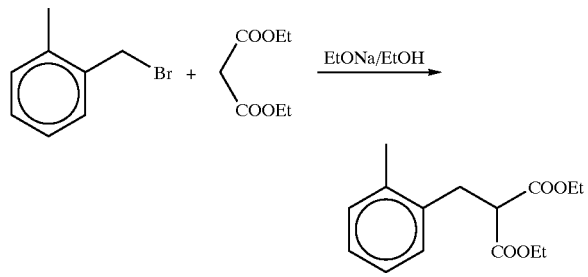

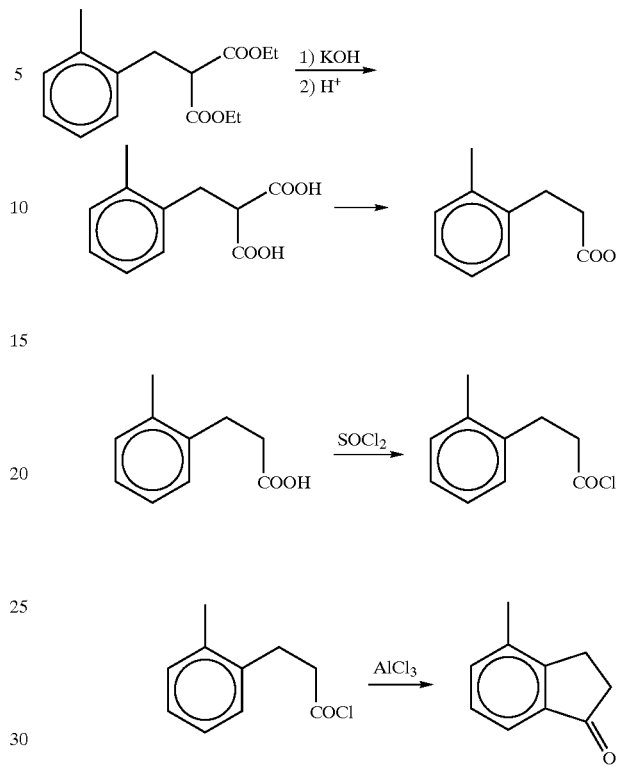

108.0 g (583.7 mmoles) of o-methylbenzylbromide
150 ml (988 mmoles) of dimethylmalonate
21.4 g (930 mmoles) of sodium
350 ml of ethyl alcohol
25 g (445 mmoles) of KOH
30 ml of thionyl chloride
38 g (285.7 mmoles) of aluminum trichloride Metal sodium is added, in portions, to the ethanol. Diethylmalonate is slowly added dropwise to the solution of sodium ethylate in ethanol, at 50° C., and then o-methylbenzylbromide is added rapidly. The mixture is kept under stirring at boiling point for 2 hours. After evaporating most of the ethanol, the mixture is poured into water and is extracted with ethyl ether; after anhydrifying on $Na_2SO_4$, the solvent is evaporated at reduced pressure. The product is purified by means of distillation (T=125° C.; P=1 mmHg). 50 g of monosubstituted diethylmalonate are thus obtained.

50 g of monosubstituted diethylmalonate dissolved in 75 ml of ethanol are added to the solution of KOH in 75 ml of water. The mixture is stirred for 4 hours at 80° C. After removing the ethanol by evaporation at reduced pressure, the mixture is acidified with HCl (1:1) and extracted with ethyl acetate. After washing the organic extracts to neutrality and anhydrifying on $Na_2SO_4$, the solvent is evaporated under vacuum. 37.4 g of monosubstituted malonic acid are obtained.

The diacid, thus obtained, decarboxylates in 1 hour, at 160° C. 31.6 g of mono-acid are obtained.

$SOCl_2$ is added to the acid, dropwise. The mixture is stirred for 12 hours. The acyl chloride is isolated after removing the excess thionyl chloride by means of distillation under vacuum. 31.0 g of acyl chloride are obtained.

The acyl chloride dissolved in 50 ml of methylene chloride is added, at 10° C., to the suspension of $AlCl_3$ in 400 ml of methylene chloride. The mixture is stirred for 1 hour at room temperature. It is poured into ice and extracted with ethyl ether. After washing the organic extracts to neutrality and anhydrifying on $Na_2SO_4$, the solvent is evaporated under vacuum. 22.0 g of product are obtained (total yield=26%).

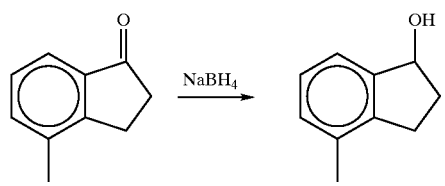

22.0 g (150.7 mmoles) of 4-methyl-1-indanone
3.9 g (102.6 mmoles) of sodium boronhydride
88 ml of tetrahydrofuran
44 ml of methanol $NaBH_4$ is added, in portions, at 0° C., to the solution of 4-methyl-1-indanone in $THF/CH_3OH$. After 3 hours the mixture is poured into water and extracted with ether. After washing the organic extracts to neutrality and anhydrifying on $Na_2SO_4$, the solvent is evaporated under vacuum. 22.0 g of 4-methyl-1-indanol are obtained (yield=99%).

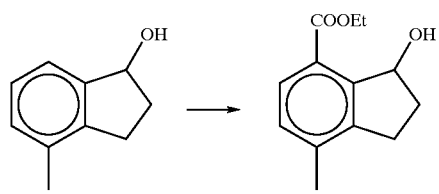

22 g (148.6 mmoles) of 4-methyl-1-indanol
123 ml (307 mmoles) of n-butyl-lithium 2.5 M solution in hexane
750 ml of hexane
39.1 ml (322 mmoles) of diethylcarbonate N-butyl-lithium is added, at 0° C., to the solution of 4-methyl-1-indanol in hexane. The mixture is stirred for 2 hours at 60° C. Diethylcarbonate is added dropwise, at −70° C. The mixture is left to rise to room temperature. After 8 hours it is poured into water and extracted with ethyl ether. After washing the organic extracts to neutrality and anhydrifying on $Na_2SO_4$, the solvent is evaporated. After purification on a silica gel chromatographic column (eluant hexane/ethyl acetate=9/1), 6.9 g of product are obtained (yield=21.2%)

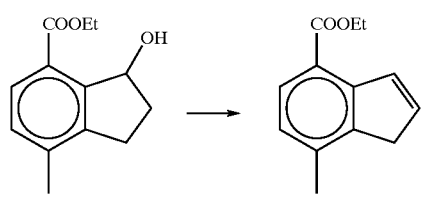

12.5 g (56.8 mmoles) of hydroxy ester
400 mg (2.1 mmoles) of p-toluenesulfonic acid (PTSA)
100 of toluene.

PTSA is added to the toluene solution of hydroxy ester. The mixture is stirred at boiling point, removing the azeotropic mixture/toluene by distillation. After 2 hours the mixture is washed until neutrality with a saturated solution of $NaHCO_3$ and anhydrified on $Na_2SO_4$, and the solvent is evaporated. 10.0 g of product are thus obtained (yield=87%).

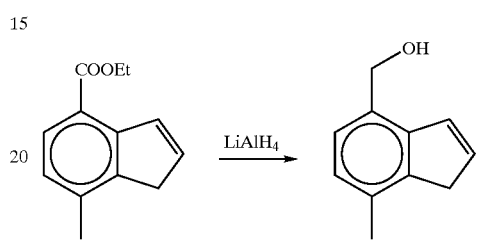

10.0 g (49.5 mmoles) of ester
1.1 g (28.9 mmoles) of lithium aluminum hydride
200 ml of ethyl ether The ester dissolved in 60 ml of ethyl ether is added, at −30° C., by means of a drip funnel, to the suspension in ethyl ether of $LiAlH_4$. After 30 minutes water is slowly added, at 0° C., and then HCl (2N); the mixture is extracted with ethyl ether. After washing the organic extracts to neutrality and anhydrifying on $Na_2SO_4$, the solvent is evaporated at reduced pressure.

7.8 g of alcohol are obtained (yield=99%).

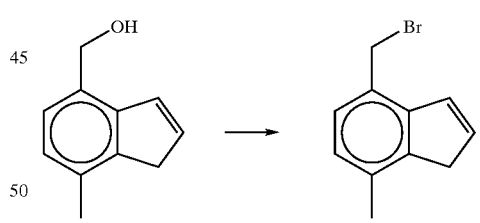

8.8 g (55 mmoles) of alcohol
1.77 ml (18.15 mmoles) of phosphorous tribromide
110 ml of methylene chloride.

$PBr_3$ is added dropwise, at −20° C., to the solution of alcohol in $CH_2Cl_2$. After 30 minutes a saturated aqueous solution of $NaHCO_3$ is slowly added until basic pH. The mixture is extracted with ethyl ether and is washed to neutrality with water. After anhydrifying on $Na_2SO_4$ and evaporating the solvent, 7.8 g of product are obtained (yield=64%).

Preparation of 4,7-dimethyl-indenyl-lithium

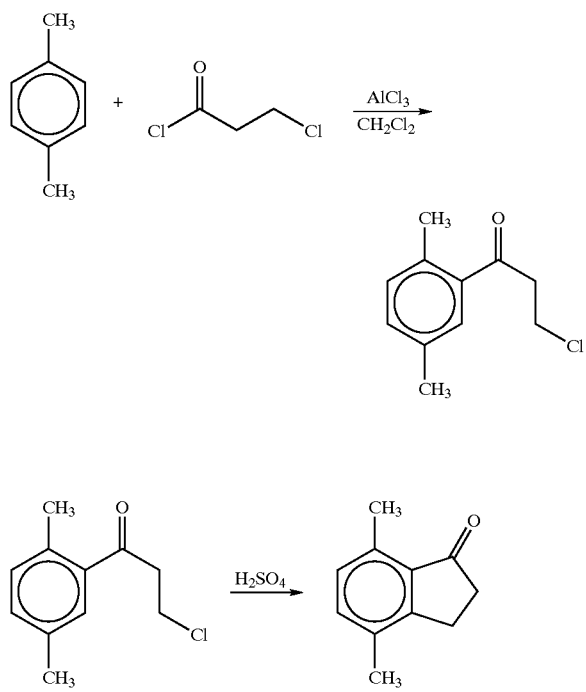

14.5 g (137 mmoles) of p-xylene
16 g of AlCl$_3$
10 ml (104.7 mmoles) of 3-chloropropionyl chloride
70 ml of methylene chloride
90 ml of conc. H$_2$SO$_4$.

A solution of 3-chloro propionyl chloride in xylene is dripped in about 1 hour into a suspension of AlCl$_3$ in methylene chloride maintained at 0° C. in an inert atmosphere. At the end of the addition the mixture is left to rise to 10° C. and is maintained at 10–20° C. for about 2 hours. It is poured into ice and extracted with methylene chloride. The organic extracts are washed with water until neutrality and then dried on sodium sulfate.

The residue obtained by evaporation of the solvent is added to H$_2$SO$_4$ at such a rate as to maintain the temperature between 20 and 30° C. At the end of the addition the mixture is brought to 80° C. and maintained at this temperature for 2 hours. The mixture is then poured into ice and is extracted with ethyl ether. ether solution is washed to neutrality with a saturated solution of sodium bicarbonate and then water, and is dried on sodium sulfate. The solid obtained by evaporation of the ether is washed with petroleum ether and dried. 20 g of 4,7-dimethyl-1-indanone are thus obtained (91% of yield in the two passages).

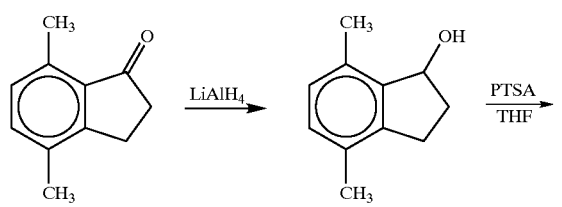

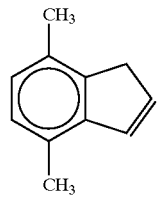

2.9 g (18.1 mmoles) of 4,7-dimethyl-1-indanone
0.35 g (9.2 mmoles) of LiAlH$_4$
30 ml of ethyl ether
10 ml of THF
0.2 g (1.05 mmoles) of p-toluenesulfonic acid (PTSA).

Indanone is slowly added to the suspension of LiAlH$_4$ maintained at −30° C. in an inert atmosphere. After 30 minutes the reaction is completed. Ice and HCl 2N are carefully added, the mixture is then extracted with ethyl ether and washed to neutrality, dried on sodium sulfate and evaporated. The indanol obtained is dissolved in 10 ml of THF, p-toluenesulfonic acid is added and the mixture is brought to reflux temperature for 1 hour. Solid NaHCO$_3$ and Na$_2$SO$_4$ are added. The mixture is filtered and the solvent evaporated obtaining 2.4 g of 4,7-dimethylindene (91% yield).

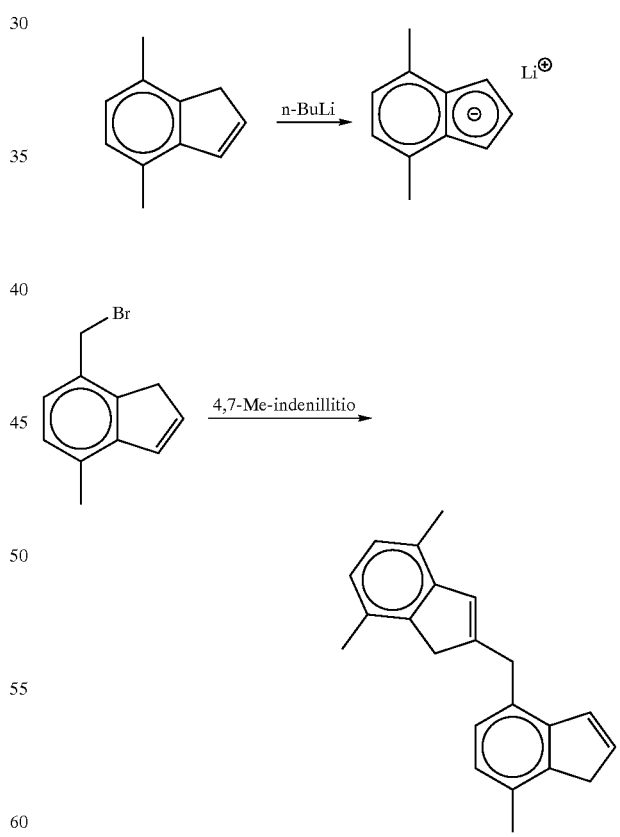

7.4 g (51.4 mmoles) of 4,7-dimethyl-indene
32.3 ml (51.6 mmoles) of LiBu 1.6 M solution in hexane
7.8 g (35.1 mmoles) of benzyl bromide
297 ml of tetrahydrofuran
148 ml of hexane LiBu is added to the solution in THF and hexane of 4,7-dimethyl-indene. After 2 hours, the bromide dissolved in 20 ml of THF and 10 ml of hexane is added, at −70° C. The mixture is left to rise to room temperature, after 8 hours water is added and the mixture is extracted with ethyl ether. After washing the organic extracts to neutrality and anhydrifying on Na$_2$SO$_4$, the solvent is evaporated. 3.1 g of product are obtained, after purification on a silica gel column using hexane/ethyl acetate as eluant in a ratio of 98/2 (yield=31%).

EXAMPLE 4

Synthesis of 4-methylene(2-indenyl)indene

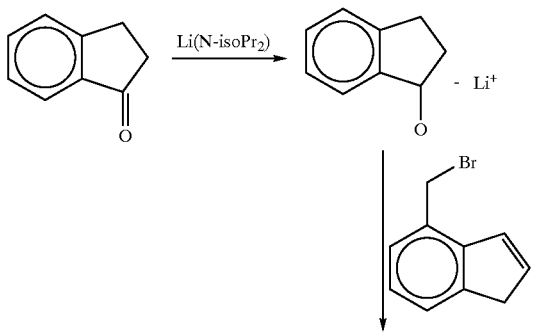

11.2 ml (79.8 mmoles) of diisopropylamine
29 ml (72.5 mmoles) of LiBu 2.5 M solution in hexane
9.5 g (72 mmoles) of 1-indanone
6.0 g (28.8 mmoles) of 4-bromethylindene LiBu is added dropwise to the solution of diisopropylamine in 70 ml of THF, at −20° C. After 40 minutes a 2 M solution of 1-indanone in THF is added, at −70° C. After 90 minutes a 2 M solution of 4-bromoethylindene (prepared as described in example 2) in THF is added. The mixture is left to rise to room temperature. After 30 minutes it is poured into water and extracted with ethyl ether. After washing the organic extracts to neutrality, with a saturated aqueous solution of NH$_4$Cl and with water, they are anhydrified on Na$_2$SO$_4$ and the solvent is evaporated. 14 g of raw 4-methylene( 2-indan-1-one)indene are obtained.

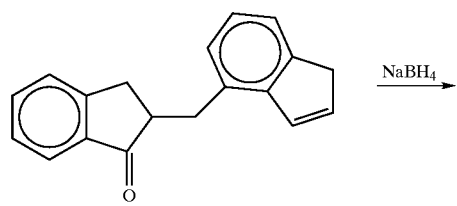

-continued

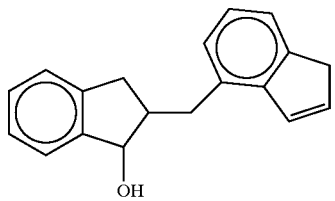

13.8 g of raw 4-methylene(2-indan-1-one)indene
2.6 g (68.42 mmoles) of sodium borohydride
120 ml of tetrahydrofuran
60 ml of hexane.

NaBH$_4$ is added to the solution in THF and hexane of 1-indanone-2-substituted, at −20° C. The mixture is left to rise to room temperature. After 2 hours water is added and the mixture is extracted with ethyl ether. After washing the organic extracts to neutrality with a saturated aqueous solution of NH$_4$Cl and anhydrifying on Na$_2$SO$_4$, the solvent is evaporated. 13.0 g of raw 4-methylene(2-indan-1-ol)indene are obtained.

13.0 g of raw 4-methylene(2-indan-1-ol)indene
15.0 g of anhydrous copper sulfate
100 ml of toluene.

The alcohol is added to the suspension of CuSO$_4$ in toluene. After 90 minutes at 110° C. the mixture is poured into water and extracted with ethyl ether. After washing the organic extracts to neutrality with water and anhydrifying on Na$_2$SO$_4$, the solvent is evaporated. 1.8 g of 4-methylene(2-indenyl)indene are obtained, after purification on a silica gel column (eluant: hexane/ethyl acetate=99/1).

EXAMPLE 5

Synthesis of 1-methyl-4-methylene(1-η⁵-indenyl)-η⁵-indenyl)-η⁵-indenyl zirconium dichloride

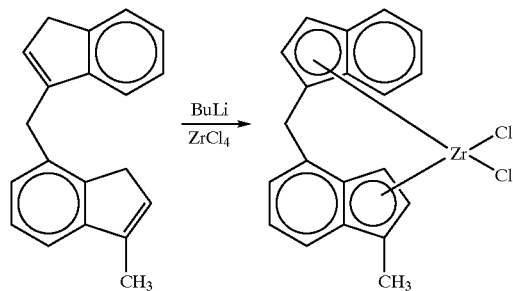

2.4 g (9.3 mmoles) of 1-methyl-4-methylene(1-indenyl) indene
15 cc (24 mmoles) of LiBu 1.6 M in hexane
80 cc of ethyl ether
1.7 g (5.6 mmoles) of $ZrCl_4$.

LiBu is added, by means of a drip funnel, to the ether solution of 1-methyl-4-methylene(1-indenyl)indene; approximately half-way through the addition the corresponding lithium salt begins to precipitate. The solution is dark yellow whereas the precipitate is white. The mixture is left under stirring for a night. A DCI control (sample treated with methyl iodide) shows the presence of ligand, mono-salt and di-salt, in approximately equimolar quantities. A further 10 cc of LiBu are added. GC mass analysis reveals the presence of the di-salt with traces of mono-salt and the absence of the ligand. The mixture is left under stirring for 1 night.

The lithium salt is decanted, washed several times with hexane and finally dried under vacuum. The solid is suspended in about 80 cc of toluene, cooled to −70° C. and then zirconium tetrachloride is added. The temperature is left to rise spontaneously to room value and the mixture is left under stirring for a further 30 minutes. The suspension (dark red) is filtered and washed with toluene (3×10 ml) and subsequently with methylene chloride (3×10 ml).

The filtrate is concentrated, the formation of pitchy products is observed, which are separated by filtration. The limpid solution is dried, and ethyl ether is added to the residue obtained. There is the initial formation of a solution from which the complex is separated in the form of a yellow solid.

¹H-NMR (ppm rel. to TMS).
7.50–7.15 (m, 4H), 7.13–6.90 (m, 3H), 6.73 (d, 1H, J= 3.1 Hz), 6.63 (d, 2H, J=2.6 Hz), 6.54 (d, 1H, J= 3.0 Hz), 4.53 (d, 1H, J=14.0 Hz), 4.32 (d, 1H, J= 14.0 Hz), 2.44 (s, 3H).

EXAMPLES 6–9

Copolymerization of ethylene/propylene

Examples 6 to 9 refer to a series of copolymerization tests for the preparation of elastomeric polymers of the EPR type based on ethylene/propylene, carried out using a catalytic system comprising on the one hand the metallocene complex 1-methyl-4methylene (1-η⁵-indenyl)-η⁵-indenyl zirconium dichloride, obtained as described above in example 5 and methylalumoxane (MAO) as cocatalyst. The specific polymerization conditions of each example and the results obtained are indicated in Table 1 below, which specifies in succession, the reference example number, the quantity of zirconium used, the atomic ratio between aluminum in MAO and zirconium, the total polymerization pressure, the activity of the catalytic system with reference to the zirconium, the relative quantity, by weight, of the $C_3$ monomeric units in the polymer, the weight average molecular weight $M_w$ and the molecular weight dispersion $M_w/M_n$.

The polymerization is carried out in a 0.5 liter pressure reactor, equipped with a magnetic anchor drag stirrer and an external jacket connected to a heat exchanger for the temperature control. The reactor is previously flushed by maintaining under vacuum (0.1 Pascal) at a temperature of 80° C. for at least 2 h.

120 g of liquid "polymerization grade" propylene are fed into the reactor at 23° C. The reactor is then brought to the polymerization temperature of 40° C. and, "polymerization grade" gaseous ethylene is fed by means of a plunged pipe until the desired equilibrium pressure (2.0–2.7 MPa) is reached. Under these conditions the molar concentration of ethylene in the liquid phase ranges from 11 to 23%, depending on the total pressure of the system, as can be easily calculated using the appropriate liquid-vapor tables.

MAO, as a 1.5 M solution (as Al) in toluene (commercial product Eurecene 5100 10T of Witco) and the desired quantity of the above metallocene complex, as a toluene solution having a concentration generally ranging from $3\times10^{-4}$ to $1\times10^{-3}$ M, are charged into a suitable tailed test-tube, maintained under nitrogen. The catalyst solution thus formed is maintained at room temperature for a few minutes and is then transferred under a stream of inert gas to a metal container from which it is introduced into the reactor, by means of an overpressure of nitrogen.

The polymerization reaction is carried out at 40° C., care being taken that the total pressure is kept constant by continuously feeding ethylene to compensate the part which has reacted in the meantime. After 15 minutes the feeding of ethylene is interrupted and the polymerization is stopped by the rapid degassing of the residual monomers. The polymer is recovered, after washing it with ethyl alcohol and drying at 60° C., 1000 Pa, for at least 8 h. The solid thus obtained is weighed and the catalytic activity is calculated as kilograms of polymer per gram of metal zirconium per hour: ($kg_{pol}/g_{zr}$×h). The content of the propylene units is measured on the dried and homogenized solid, by means of the known techniques based on IR spectroscopy, together with the weight (Mw) and number ($M_n$) average molecular weight. The results are indicated in Table 1.

EXAMPLES 10–12

Examples 10 to 12 refer to a series of copolymerization tests for the preparation of elastomeric polymers of the EPR type based on ethylene/propylene using a catalytic system comprising the metallocene complex, obtained as described above in example 5, an aluminum alkyl and an appropriate compound of boron as cocatalyst.

The procedure described in examples 6–9 is followed with the following variations:

About 120 g of "polymerization grade" liquid propylene and the exact quantity of Al(iso-Bu)₃ are fed into the reactor at 23° C., so as to obtain a concentration of aluminum equal to $5\times10^{-3}$ moles/liter. The reactor is then brought to polymerization temperature of 40° C. and "polymerization grade" gaseous ethylene is fed by means of a plunged pipe, until the desired equilibrium pressure (2.2–2.7 MPa) is reached. Under these conditions the molar concentration of ethylene in the liquid phase ranges from 12 to 23%, depending on the total pressure of the system, as can be easily calculated using the appropriate liquid-vapor tables.

Al(iso-Bu)$_3$ as an 0.4 M solution in toluene and the desired quantity of metallocene complex, prepared as described in example 5, as a toluene solution having a concentration generally ranging from $3\times10^{-4}$ to $1\times10^{-3}$ M, are charged into a suitable tailed test-tube, maintained under nitrogen. The solution thus obtained is maintained under stirring at 23° C. for 15 minutes after which a toluene solution, having a concentration generally ranging from $5\times10^{-4}$ to $1\times10^{-3}$ M, of [CPh$_3$][B(C$_6$F$_5$)$_4$] is added and, after a few minutes, it is transferred under a stream of inert gas to a metal container from which it is introduced into the reactor, by means of an overpressure of nitrogen. The results are indicated in Table 2.

carbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements; wherein any two, or both pairs, of the substituents $R_3$, $R_4$, $R_5$ and $R_6$, adjacent to each other, may be joined to each other to form a saturated or unsaturated $C_4$–$C_{20}$ cyclic structure, comprising a bond of the cyclopentadienyl ring, said structure optionally containing one or more heteroatoms;

M represents titanium, zirconium or hafnium;

$X_1$ and $X_2$ each independently represent an anionic group bound to the metal M, wherein $X_1$ and $X_2$ may be chemically bound to each other to form a cycle having from 4 to 7 atoms different from hydrogen, also comprising the metal M.

TABLE 1

$C_2/C_3$ copolymerization tests with a catalytic system composed of 1-methyl-4-methylene(1-$\eta^5$-indenyl)-$\eta^5$-indenyl zirconium dichloride and MAO

| Example Nr. | Zr (moles × 10$^6$) | Al/Zr (mol/mol) | P$_{total}$ (MPa) | Activity (kg$_{pol.}$/g$_{Zr}$ × h) | C$_{3(polymer)}$ (weight %) | M$_w$ (× 10$^3$) | M$_w$/M$_n$ |
|---|---|---|---|---|---|---|---|
| 6 | 1.75 | 1975 | 2.0 | 218 | 62 | 89 | 2.8 |
| 7 | 1.30 | 2385 | 2.2 | 806 | 55 | 134 | 2.9 |
| 8 | 0.65 | 3950 | 2.5 | 3275 | 44 | 208 | 2.4 |
| 9 | 0.38 | 5980 | 2.7 | 6070 | 39 | 317 | 2.2 |

TABLE 2

$C_2/C_3$ copolymerization tests carried out using the catalytic system composed of 1-methyl-4-methylene(1-$\eta^5$-indenyl)-$\eta^5$-indenyl zirconium dichloride, Al(iso-Bu)$_3$ and CPh$_3$[B(C$_6$F$_5$)$_4$].

| Example Nr. | Zr (moles × 10$^6$) | Al/Zr (mol/mol) | B/Zr (mol/mol) | P$_{total}$ (MPa) | Activity (kg$_{pol.}$/g$_{Zr}$ × h) | C$_{3(polymer)}$ (weight %) | M$_w$ (× 10$^3$) | M$_w$/M$_n$ |
|---|---|---|---|---|---|---|---|---|
| 10 | 1.1 | 350 | 1.1 | 2.2 | 567 | 48 | 162 | 3.1 |
| 11 | 0.9 | 350 | 1.1 | 2.5 | 1758 | 41 | 237 | 2.6 |
| 12 | 0.6 | 350 | 1.1 | 2.7 | 2749 | 35 | 330 | 2.4 |

What is claimed is:

1. A metallocene compound having formula (I):

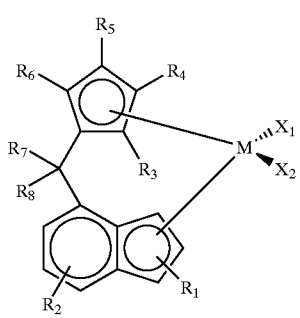

(I)

wherein:
R$_1$ and R$_2$ can independently occupy any of the free positions of the indene group;
R$_1$, R$_2$, R$_3$, R$_4$, R$_5$, R$_6$, R$_7$ and R$_8$ independently represent hydrogen, halogen, a linear or branched, saturated or unsaturated, cycloaliphatic or aromatic $C_1$–$C_{20}$ hydro- 2. The metallocene compound of claim 1, wherein the halogen is selected from the group consisting of F, Cl and Br.

3. The metallocene compound of claim 1, wherein the heteroatom is selected from the group consisting of Si, O, N, S and P.

4. A metallocene compound having formula (I),

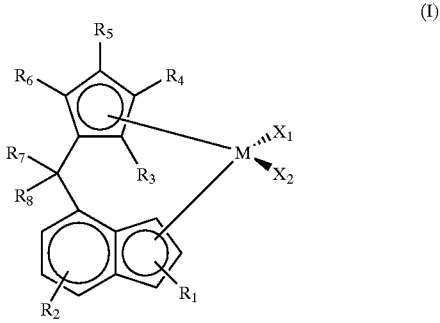

(I)

wherein
- $R_1$ and $R_2$ can independently occupy any of the free positions of the indene group;
- $R_1, R_2, R_3, R_4, R_5, R_6, R_7$ and $R_8$ independently represent hydrogen, halogen, a linear or branched, saturated or unsaturated, cycloaliphatic or aromatic $C_1$–$C_{20}$ hydrocarbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements; wherein any two, or both pairs, of the substituents $R_3$, $R_4$, $R_5$ and $R_6$, adjacent to each other, may be joined to each other to form a saturated or unsaturated $C_4$–$C_{20}$ cyclic structure, comprising a bond of the cyclopentadienyl ring, said structure optionally containing one or more heteroatoms;
- M represents titanium, zirconium or hafnium;
- $X_1$ and $X_2$ each independently represent an anionic group bound to the metal M, wherein $X_1$ and $X_2$ may be chemically bound to each other to form a cycle having from 4 to 7 atoms different from hydrogen, also comprising the metal M, wherein groups $X_1$ and $X_2$ are selected from chloride, methyl, ethyl, butyl, isopropyl, isoamyl, octyl, decyl, benzyl, allyl, methylallyl, cyclopentyl, cyclohexyl, 4-methylcyclohexyl, phenyl, toluyl, methoxyl, ethoxyl, iso-butoxyl, sec-butoxyl, ethylsulfide, acetate, propionate, butyrate, pivalate, versatate, naphthenate, diethylamide, dibutylamide, or bis(trimethylsilyl) amide; or wherein $X_1$ and $X_2$ are chemically bound to each other to form one or more divalent anionic groups.

5. The metallocene compound of claim 4, wherein the divalent anionic group is a trimethylene, tetramethylene or ethylenedioxy group.

6. The metallocene compound of claim 4, wherein the halogen is selected from the group consisting of F, Cl and Br.

7. The metallocene compound of claim 4, wherein the heteroatom is selected from the group consisting of Si, O, N, S and P.

8. A compound having formula (Ia):

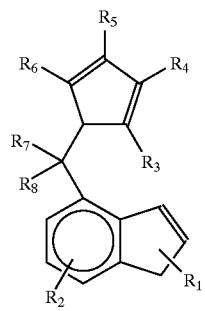

(Ia)

wherein:
- $R_1$ and $R_2$ can independently occupy any of the free positions of the indene group;
- $R_1, R_2, R_3, R_4, R_5, R_6, R_7$ and $R_8$ independently represent hydrogen, halogen, a linear or branched, saturated or unsaturated, cycloaliphatic or aromatic $C_1$–$C_{20}$ hydrocarbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements, wherein any two, or both pairs, of the substituents $R_3$, $R_4$, $R_5$ and $R_6$, adjacent to each other, may be joined to each other to form a saturated or unsaturated $C_4$–$C_{20}$ cyclic structure, comprising a bond of the cyclopentadienyl ring, said structure optionally containing one or more heteroatoms.

9. The compound according to claim 8, selected from the group consisting of:

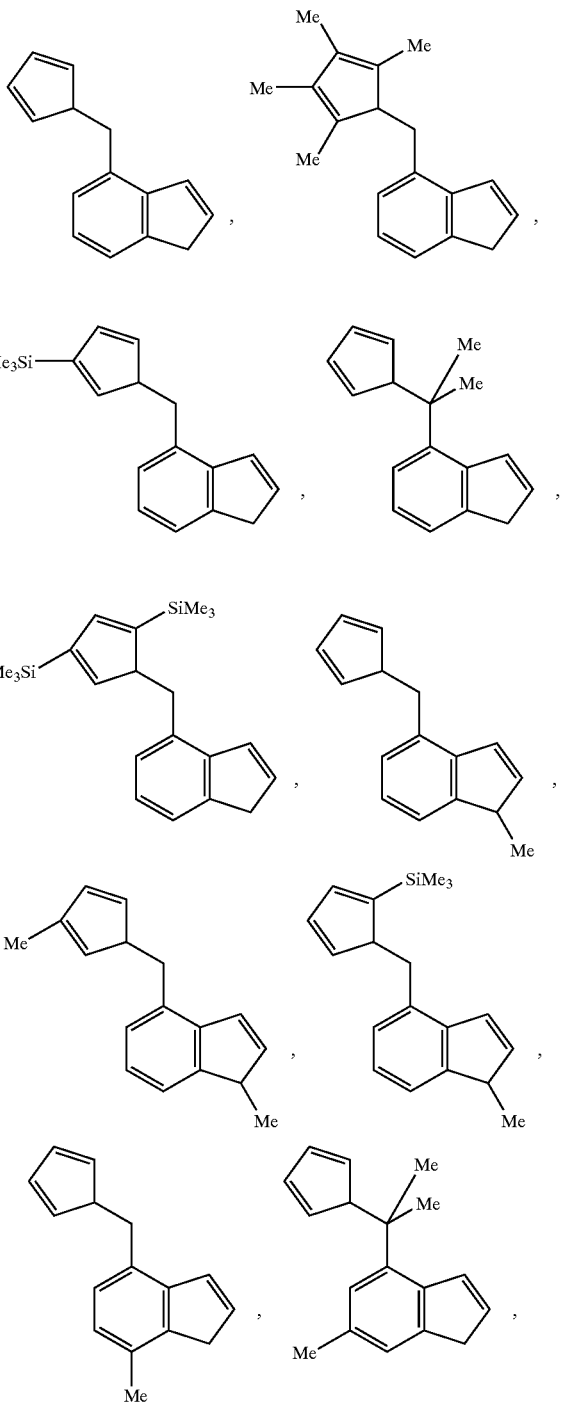

-continued
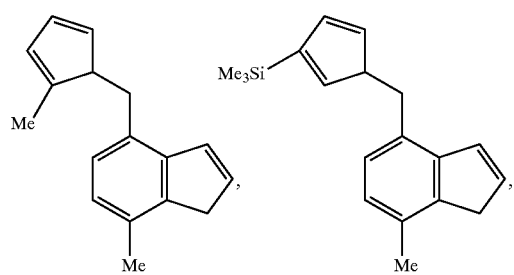
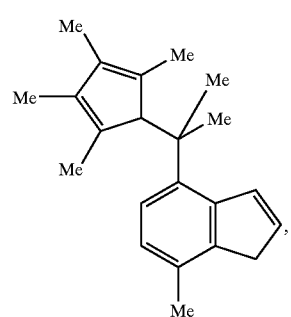
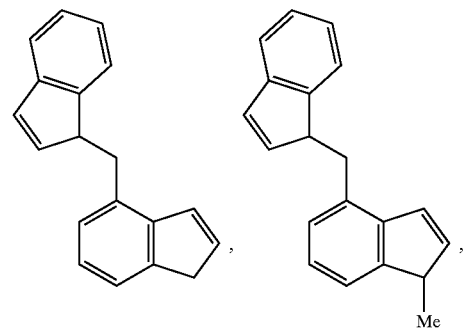
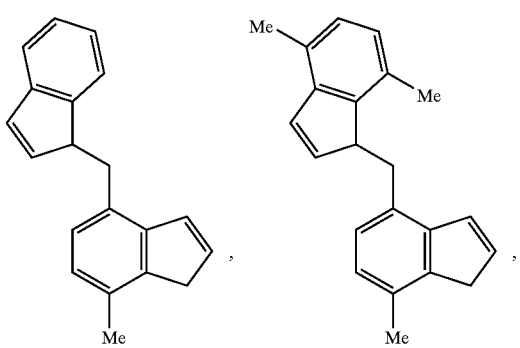
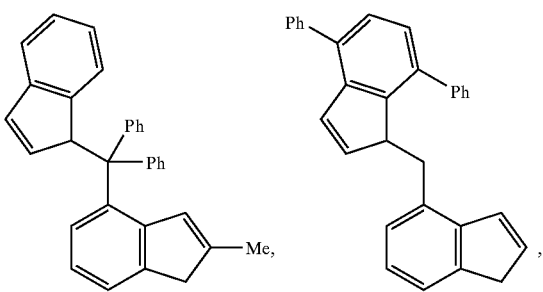
-continued
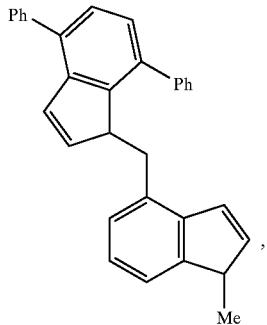
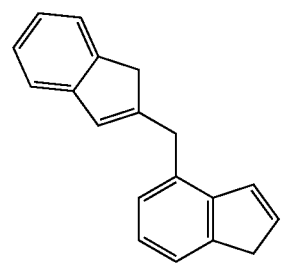
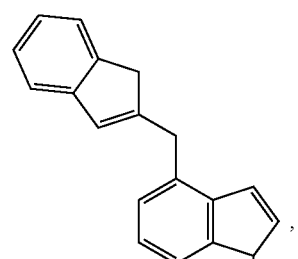
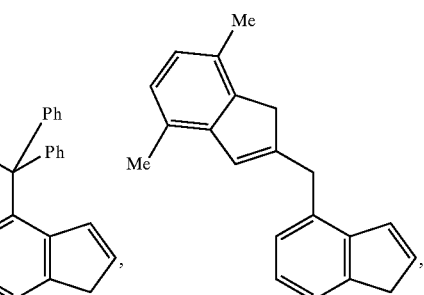
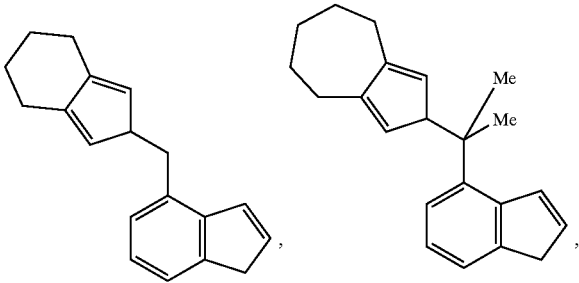

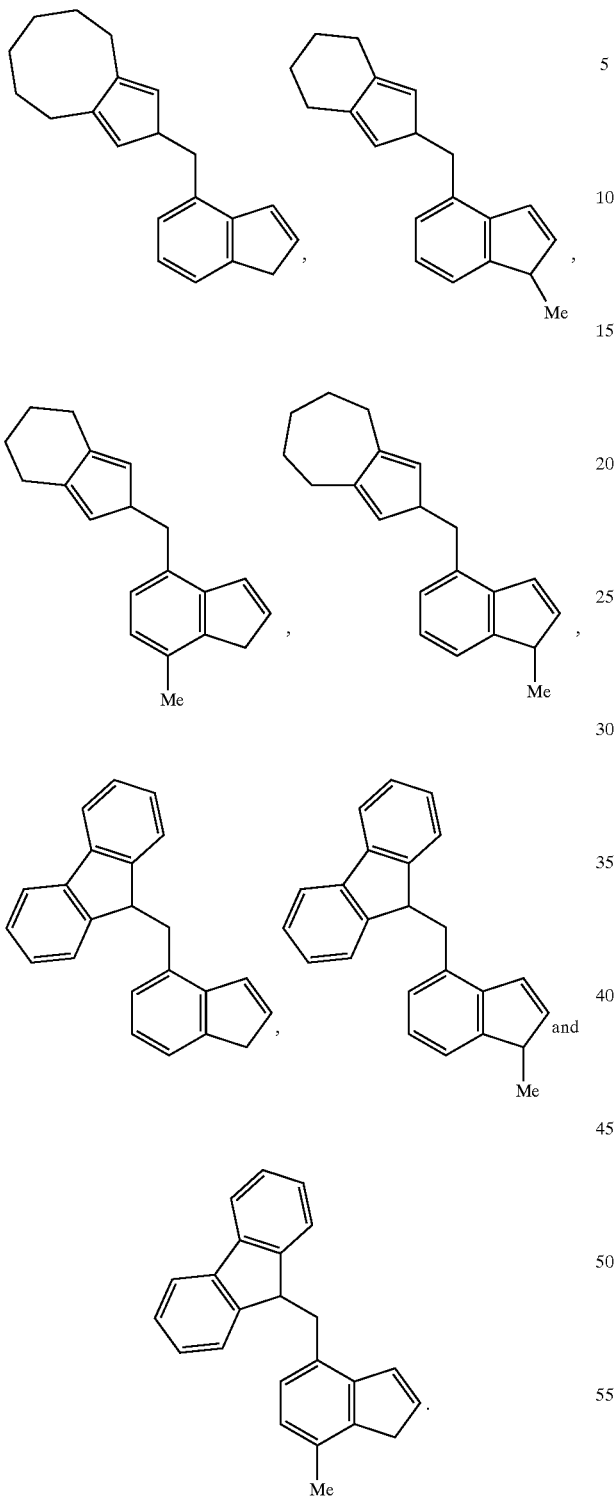

10. The compound of claim 8, wherein the halogen is selected from the group consisting of F, Cl and Br.

11. The metallocene compound of claim 8, wherein the heteroatom of Groups 14–16 of the periodic table of the elements is selected from the group consisting of Si, O, N, S and P.

12. A process for the preparation of the compound (Ia) comprising,

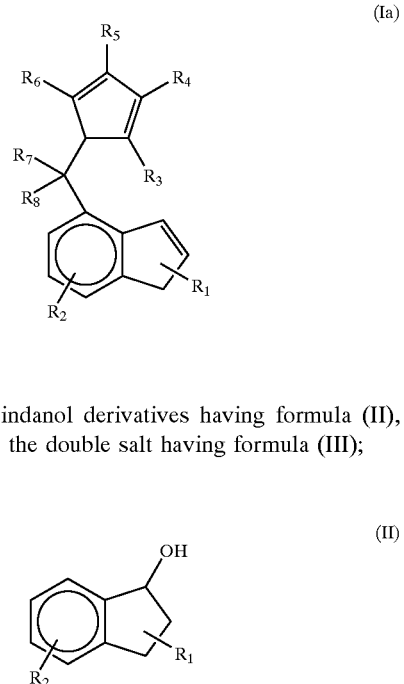

(a) reaction of 1-indanol derivatives having formula (II), with LiBu to give the double salt having formula (III);

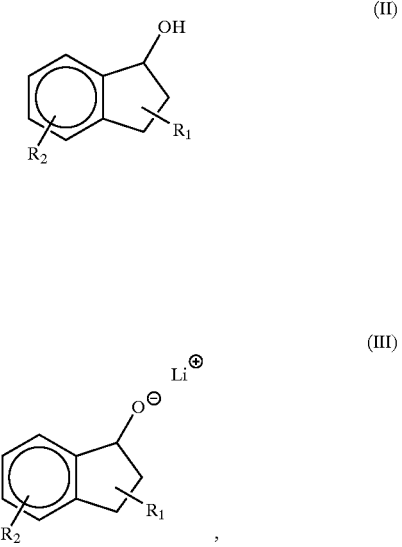

wherein $R_1$ and $R_2$ can independently occupy any of the free positions of the indene group, and $R_1$, $R_2$, $R_3$, $R_4$, $R_5$, $R_6$, $R_7$, and $R_8$ may independently represent hydrogen, halogen, a linear or branched, saturated or unsaturated, cycloaliphatic or aromatic $C_1$–$C_{20}$ hydrocarbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements, wherein any two, or both pairs, of the substituents $R_3$, $R_4$, $R_5$ and $R_6$, adjacent to each other, may be joined to each other to form a saturated or unsaturated $C_4$–$C_{20}$ cyclic structure, comprising a bond of the cyclopentadienyl ring, said structure optionally containing one or more heteroatoms;

(b) reaction of the double lithium salt having formula (III), obtained in (a), with one or more electrophilic reagents, to obtain hydroxy ester (IV);

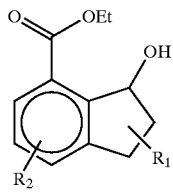

(IV)

(c) dehydration reaction of the alcohol function of the hydroxy ester (IV), obtained in (b), carried out in an acid environment to give the ester (V);

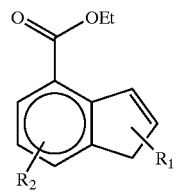

(V)

(d) reduction reaction of the ester having formula (V), obtained in (c), with the formation of alcohol (VI):

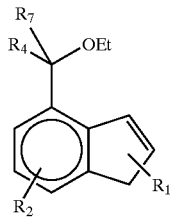

(VI)

(e) bromination reaction of the alcohol having formula (VI) to give the bromine derivative (VII);

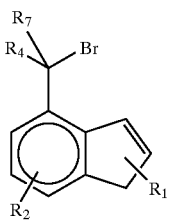

(VII)

(f) formation reaction of the indenyl cyclopentadienyl derivative having formula (Ia), starting from the bromine derivative having formula (VII) obtained in (e) and from cyclopentadienyl anions, whose corresponding neutral derivative can be represented by the following formula (VIII)

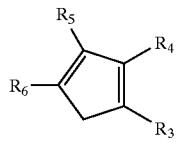

(VIII)

13. The process according to claim 12, wherein:
(a) is carried out in an organic solvent, in the presence of one or more base reagents and at temperatures of from −30° to 120° C.;
(b) is carried out in the presence of hydrocarbon and/or ether solvents or mixtures thereof at temperatures of from −100° to 120° C.;
(c) is carried out in the presence of a solvent and a strong acid at temperatures of from −25° to 150° C.
(d) is carried out in an organic solvent, with a reagent selected from the group consisting of $LiAlH_4$, $NaBH_4$, NaH, $MgH_2$, LiBu, LiMe, MeMgCl, PhMgBr, and $Bu^tMgCl$ at temperatures of from −70° to 100° C;
(e) is carried out in an organic solvent by means of a brominating agent;
(f) is carried out in a solvent selected from the group consisting of aromatic hydrocarbons, aliphatic hydrocarbons, ethers and mixtures thereof, at a temperature of from −80° to 120° C. and the cyclopentadienyl anion is obtained by the reaction of the corresponding neutral derivative, having formula (VIII), with a reagent selected from the group consisting of alkyls of electropositive metals, hydrides of electro-positive metals, Grignard reagents, alkaline metals, earth-alkaline metals and alloys of alkaline and earth-alkaline metals, in a solvent selected from the group consisting of aliphatic hydrocarbons, aromatic hydrocarbons, ethers and mixtures thereof, at temperatures of from −80° to 110°C.

14. The process according to claim 13, wherein:
(a) is carried out in hexane as solvent, in the presence of lithium butyl at temperatures of from 0° to 70° C.;
(b) is carried out in hexane as solvent at temperatures of from −70° to 25° C.;
(c) is carried out in toluene as solvent in the presence of para-toluenesulfonic acid, at temperatures of from 50 to 110° C.
(d) is carried out in ethyl ether, in the presence of $LiAlH_4$, at temperatures of from −30° to 25° C.;
(e) is carried out in methylene chloride in the presence of $PBr_3$ at temperatures of from −20° to 25° C.;
(f) the cyclopentadienyl anion is obtained by the reaction between indene or 4,7-dimethyl-indene, with lithium butyl, in mixtures of hexane/THF at temperatures of from 0° to 60° C.

15. The process of claim 13, wherein the strong acid is selected from the group consisting of HCl, $H_2SO_4$, para-toluenesulfonic acid and a blander dehydrating agent.

16. The process of claim 15, wherein the blander dehydrating agent is a silica gel.

17. The process according to claim 12, wherein (f) is carried out by reacting the brominated product (VII) with a lithium enolate to form one or more indenyl-cyclopentadienyl products having formula (XIII):

(XIII)

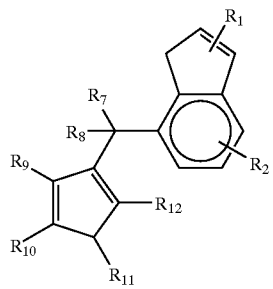

wherein:

R₁ and R₂ can independently occupy any of the free positions of the indenyl group;

$R_1$, $R_2$, $R_7$, $R_8$, $R_9$, $R_{10}$, and $R_{11}$ independently represent hydrogen, halogen, a linear or branched, saturated or unsaturated, cycloaliphatic or aromatic $C_1$–$C_{20}$ hydrocarbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements; or, wherein any two of the substituents $R_9$, $R_{10}$ and $R_{11}$, adjacent to each other, may be joined to each other to form a saturated or unsaturated $C_4$–$C_{20}$ cyclic structure, comprising a bond of the cyclopentadienyl ring, said structure optionally containing one or more heteroatoms;

$R_{12}$ can be independently hydrogen, a linear or branched, saturated or unsaturated, cycloaliphatic or aromatic $C_1$–$C_{20}$ hydrocarbyl group, or a $C_1$–$C_{20}$ hydrocarbyl group comprising one or more heteroatoms of groups 14 to 16 of the periodic table of elements;

said process further comprising (g) reaction of a cyclic ketone having formula (IX), with a lithium amide to form a mixture of one or more anions having formula (Xa)/(Xb);

(IX)

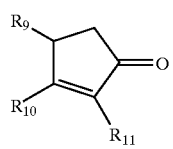

(Xa)

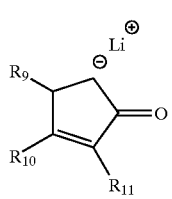

(Xb)

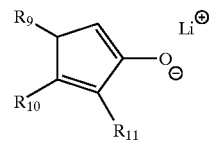

(h) reaction of the mixture of anions (Xa)/(Xb) with the brominated product having formula (VII), prepared according to (g) to form (XI);

(XI)

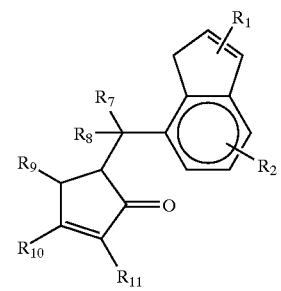

(i) reduction of the functional carbonyl group to alcohol with the formation of the derivative having formula (XII), (XII)

(j) dehydration of the derivative having formula (XII), obtained in (i), with the formation of the indenyl-cyclopentadienyl compound, having formula (XIII).

18. The process of claim 17, wherein the halogen is selected from the group consisting of F, Cl and Br.

19. The process of claim 17, wherein the heteroatom is selected from the group consisting of Si, O, N, S and P.

20. The process of claim 12, wherein the electrophilic reagent is diethyl carbonate.

21. The process of claim 12, wherein the halogen is selected from the group consisting of F, Cl and Br.

22. The process of claim 12, wherein the heteroatom is selected from the group consisting of Si, O, N, S and P.

23. The process according to claim 12, wherein the cyclopentadienyl anion is obtained by the reaction of the corresponding neutral derivative, having formula (VIII), with a reagent selected from the group consisting of alkyls of lithium, lithium hydride and lithium metal.

24. A catalyst for the polymerization of olefins comprising a reaction product between:

(A) one or more metallocene compounds having formula (I), free or supported on inert solids; and

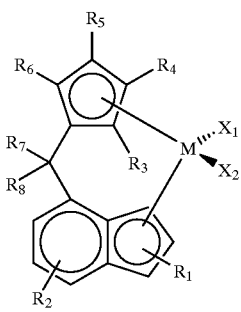

(B) one or more compounds capable of forming a metallocene alkyl cation, wherein:

$R_1$ and $R_2$ can independently occupy any of the free positions of the indene group;

$R_1$, $R_2$, $R_3$, $R_4$, $R_5$, $R_6$, $R_7$ and $R_8$ independently represent hydrogen, halogen, a linear or branched, saturated or unsaturated, cycloaliphatic or aromatic $C_1$–$C_{20}$ hydrocarbyl group, or a $C_1$–$C_{20}$ hydrocarbyl group substituted with one or more halogen atoms, or a $C_1$–$C_{20}$ hydrocarbyl group comprising one or more heteroatoms of groups 14 to 16 of the periodic table of elements; wherein any two, or both pairs, of the substituents $R_3$, $R_4$, $R_5$ and $R_6$, adjacent to each other, may be joined to each other to form a saturated or unsaturated $C_4$–$C_{20}$ cyclic structure, comprising a bond of the cyclopentadienyl ring, said structure optionally containing one or more heteroatoms;

M represents titanium, zirconium or hafnium;

$X_1$ and $X_2$ each independently represent an anionic group bound to the metal M, wherein $X_1$ and $X_2$ may be chemically bound to each other to form a cycle having from 4 to 7 atoms different from hydrogen, also comprising the metal M.

25. The catalyst for the polymerization of olefins according to claim 24, wherein the compound B is an aluminoxane.

26. The catalyst of claim 24, wherein the halogen is selected from the group consisting of F, Cl and Br.

27. The catalyst of claim 24, wherein the heteroatom is selected from the group consisting of Si, O, N, S and P.

28. A process for the preparation of the catalyst according to claim 24, comprising contacting the components (A) and (B) with each other at temperatures of from 20° to 60° C. and for times from 10 seconds to 1 hour, in a hydrocarbon medium and in a proportion that the atomic ratio between the aluminum in the aluminoxane and the transition metal M is within the range of 10 to 10000.

29. The process of claim 25, wherein the atomic ratio between the aluminum in the alumoxane and the transition metal M is from 100 to 5,000.

30. A process for the polymerization of olefins, comprising polymerizing one or more olefinic monomers in the presence of the catalyst as defined in claim 25.

31. The process according to claim 30, wherein one or more olefinic monomers are polymerized in the presence of a metallocene having formula (I) and methylalumoxane (MAO) as a cocatalyst.

32. The process according to claim 31, wherein the olefinic monomers are polymerized in the presence of a metallocene having formula (I), an aluminum alkyl and a boron compound as a cocatalyst.

33. The process according to claim 32, wherein the olefinic monomers are selected from the group consisting of ethylene, propylene and mixtures thereof.

34. The process of claim 31, wherein the olefinic monomers are selected from the group consisting of ethylene, propylene and mixtures thereof.

* * * * *